(12) United States Patent
Mansfield et al.

(10) Patent No.: US 12,257,065 B2
(45) Date of Patent: Mar. 25, 2025

(54) TECHNIQUES FOR PATIENT PRESSURE INJURY PREVENTION

(71) Applicant: The Regents of the University of California, Oakland, CA (US)

(72) Inventors: Samuel Mansfield, Santa Cruz, CA (US); Katia Obraczka, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 523 days.

(21) Appl. No.: 17/455,332

(22) Filed: Nov. 17, 2021

(65) Prior Publication Data

US 2022/0151545 A1 May 19, 2022

Related U.S. Application Data

(60) Provisional application No. 63/114,684, filed on Nov. 17, 2020.

(51) Int. Cl.
*A61B 5/11* (2006.01)
*A61B 5/00* (2006.01)

(52) U.S. Cl.
CPC ............ *A61B 5/445* (2013.01); *A61B 5/1116* (2013.01); *A61B 5/6813* (2013.01); *A61B 5/742* (2013.01); *A61B 2562/0247* (2013.01); *A61B 2562/046* (2013.01)

(58) Field of Classification Search
CPC .... A61B 2562/0247; A61B 2562/0219; A61B 5/742; A61B 5/7282; A61B 5/4836; A61B 5/1116; A61B 5/1118; A61B 2090/064; A61B 5/6843; A61B 5/11; A61B 5/6801; A61B 5/1114; A61B 5/1121; A61B 5/00; A61B 5/25; A61B 5/0036; A61B 5/067; A61B 5/02; A61B 5/684; A61B 5/0082; A61B 5/0048; A61B 5/0225; A61B 5/6886; A61B 5/1109; A61B 5/061; A61N 1/0476; A61N 1/0492; A61N 1/02; A61N 1/0408; A61N 1/36; A61N 1/0597
See application file for complete search history.

(56) References Cited

U.S. PATENT DOCUMENTS

2017/0360357 A1* 12/2017 Larson ................. A61B 5/1115

* cited by examiner

*Primary Examiner* — Deborah L Malamud
(74) *Attorney, Agent, or Firm* — Schwegman Lundberg & Woessner, P.A.

(57) ABSTRACT

Techniques for patient pressure injury prevention (PPIP) include receiving, from a plurality of pressure sensors configured to be disposed in a spatial arrangement in contact with a patient, samples that indicate pressure measurements by the plurality of sensors at each of a plurality of different times. At each of the plurality of different times an angular orientation of the pressure is determined based on the samples. A change in the angular orientation of the pressure is determined at each successive time of the plurality of different times. A value of a patient movement parameter is determined based on the change in angular orientation of the pressure. A pressure injury category for the patient based on the value of the patient movement parameter is presented on a display device for a caregiver. Treatment of the patient by the caregiver is based on the pressure injury category.

19 Claims, 15 Drawing Sheets

TECHNIQUES FOR PATIENT PRESSURE INJURY PREVENTION

CROSS-REFERENCE TO RELATED APPLICATIONS

This application claims benefit of Provisional Appln. 63/114,684, filed Nov. 17, 2020, the entire contents of which are hereby incorporated by reference as if fully set forth herein, under 35 U.S.C. § 119(e).

STATEMENT OF GOVERNMENTAL INTEREST

This invention was made with Government support under Grant No. CNS 132115, awarded by the National Science Foundation. The Government has certain rights in the invention.

BACKGROUND

The healthcare industry has placed significant effort in reducing pressure injuries (including injuries commonly known as "bed sores") as they often occur while patients are seeking treatment for an unrelated condition, lengthen the stay of the patient, impact treatment options, are extremely painful, and can result in death. Current work has shown that an increase in nursing care can be prophylactic to reduce pressure injury occurrence. However, extraneous nursing care is not sustainable; and this limited resource is best spent on patients at greater risk. The Braden Scale is the current method of stratifying patients by four categories of risk that they would form a pressure injury. However, previous work has shown that the Braden Scale is not an accurate predictor of pressure injury formation.

SUMMARY

Techniques are provided for patient monitoring for pressure injuries. By assessing the current pressure readings in real-time, or at least with suitably low latency, on the order of an hours or less, and employing an objective metric of mobility, one can automatically determine when a patient is mobile, or conversely at risk, and automatically present this data to a caregiver in the clinic. As used herein, a patient is a human or animal subject whose condition is being monitored by a care provider.

According to a first set of embodiments, a method executed on a processor for patient pressure injury prevention (PPIP) includes receiving, from a plurality of pressure sensors configured to be disposed in a spatial arrangement in contact with a patient, samples that indicate pressure measurements by the plurality of sensors at each of a plurality of different times. The method also includes determining at each of the plurality of different times an angular orientation of the pressure based on the samples and determining a change in the angular orientation of the pressure at each successive time of the plurality of different times. Furthermore, the method includes determining a value of a patient movement parameter based on the change in angular orientation of the pressure. Still further, the method includes presenting on a display device a pressure injury category for the patient based on the value of the patient movement parameter. Treatment of the patient by a caregiver is based on the pressure injury category.

In some embodiments of the first set, the spatial arrangement of the plurality of pressure sensors is a two dimensional array, such as a 4×4 array, or contact with the patient is contact with a surface of the patient in a vicinity of a sacrum of the patients, or both.

In some embodiments of the first set, the angular orientation is a pressure plane determined by three pressure values based on the samples. In some of these embodiments, each of the three pressure values is an average of samples from a different one of three different subsets of the plurality of pressure sensors. In some of these latter embodiments, a union of the three different subsets include all of the plurality of pressure sensors, or no pressure sensor is in more than one subset of the three different subsets, or each pressure sensor in one subset is adjacent to another pressure sensor in the one subset.

In some embodiments of the first set, the angular orientation is a posture of the patient.

In some embodiments of the first set, a movement is a change in angular orientation greater than a threshold change and the patient movement parameter is based on a movement. In some of these embodiments, the patient movement parameter is a number of movements per unit time, or the patient movement parameter is a size of the movement, or both.

In some embodiments of the first set, the treatment includes movement of the patient by the caregiver at a time based on the pressure injury category.

In other sets of embodiments, a non-transitory computer-readable medium or an apparatus or system is configured to perform one or more steps of one or more of the above methods or to provide data structures to support one or more of the above methods.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

Embodiments are illustrated by way of example, and not by way of limitation, in the figures of the accompanying drawings in which like reference numerals refer to similar elements and in which.

DETAILED DESCRIPTION

A method and apparatus are described for patient pressure injury monitoring and prevention (PIMAP). In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Although embodiments are described below in the context of a particular array of pressure sensors on a human patient and a particular measure of mobility on a particular cloud system, in other embodiments, other pressure sensors, and other metrics of mobility and posture are used for either human or non-human patients on local or cloud-based systems.

1. Overview

1.1 PPIP Structures

Figure 1:
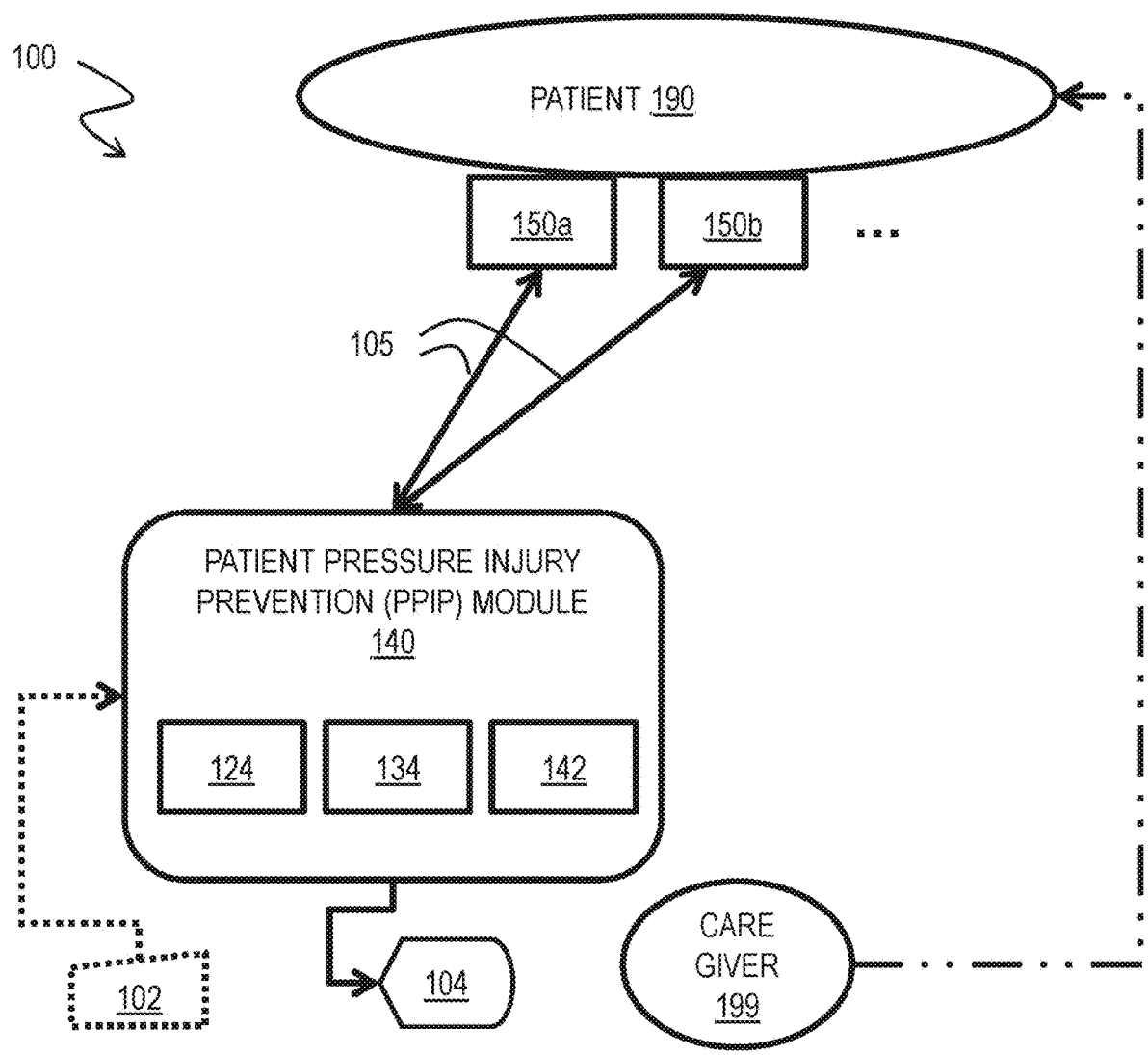
FIG. 1 is a block diagram that illustrates an example patient pressure injury prevention (PPIP) system, according to an embodiment.

FIG. 1 is a block diagram that illustrates an example patient pressure injury prevention (PPIP) system 100, according to an embodiment. Although a patient 190 and caregiver 199 are depicted in FIG. 1 so that the use of the system can be illustrated, neither the patient 190 nor the caregiver 199 is part of system 100. The system 100 includes a plurality of pressure sensors 150a, 150b, among other indicated by ellipsis, collectively referenced hereinafter as pressure sensors 150, that are disposed in a spatial arrangement in contact with a patient 190. The multiple sensors 150 are disposed so that, as the patient 190 changes posture or position, one or more sensors experience changes in pressure. For example, the sensors ae disposed in a flat or curved array that is configured to be attached to a part of the patient's body, such as in a dressing applied to a leg or torso of the patient. For example, the sensors are included in a dressing or harness configured to be attached to a patient's ankle, shin, knee, thigh, buttock, abdomen, lower back (sacrum), upper back (shoulder blade), chest, shoulder, upper arm, elbow, lower arm, or head, or some combination.

The sensors are configured to report their pressure measurements as samples data at each of multiple different times to a patient pressure injury prevention (PPIP) module 140. In some embodiments, this module 140 includes a data structure 142 with information about the sensor suite, such as format of the samples data and commands to start, stop, and change the operating range or sampling rate of each of the sensors, or some combination. Samples data reports and commands are exchanged over one or more wired or wireless communication lines 105 using any of one or more known, developing, or future protocols.

The PPIP module 140 also includes a data structure 124 to hold the samples data. The PPIP is further configured to determine a patient pressure injury category for the patient based on the samples, such that treatment of the patient by a caregiver is based on the pressure injury category. Example methods for determining this category are described below with reference to the flowchart in FIG. 4, with further details described with respect to an example embodiment. The category and zero or more intermediate results based on the samples data are stored in data structure 134. The PPIP module 140 is also configured to present to a caregiver 199 the category, and any samples data or any intermediate results of interest, on a display device 104, such as a fixed monitor connected by wire or a mobile device such as a tablet or cell phone connected by wireless communication lines to the module 140. In some embodiments, the operation of the module 140 or the manner or presentation on display device 104 or both is based at least in part on input from the caregiver provided at input device 102, such as a keyboard, mouse, touch screen, camera or microphone.

Although sensors 150 and data structures 124, 134, 142 and module 140 are depicted in FIG. 1 as integral units in a particular arrangement for purposes of illustration, in other embodiments, one or more data structures or modules are combined or divided among different computer platforms, called hosts, in a local or global network, or other data structures or modules are added, or the system is changed in some combination of ways. For example, in some embodiments the module 140 is arranged as a cloud-based monitoring and prevention (MAP) system, such as inventors' own work described in United State patent application entitled "Device-Insulated Monitoring of Patient Condition."

Figure 2A:
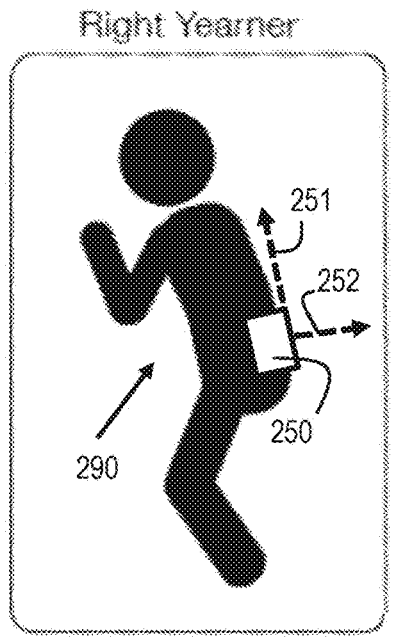
FIG. 2A through FIG. 2E are block diagrams that illustrate relationship of pressure sensors to patient posture, according to an embodiment.
Figure 2B:
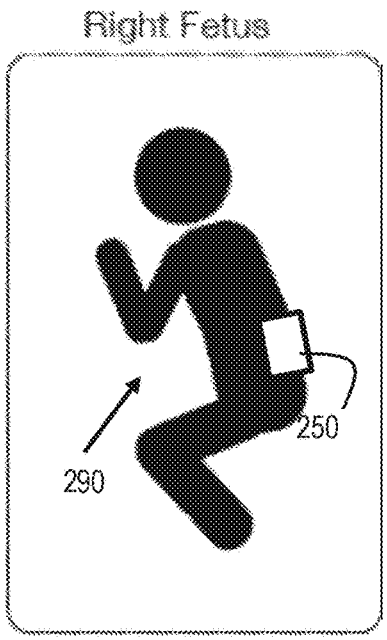
Figure 2C:
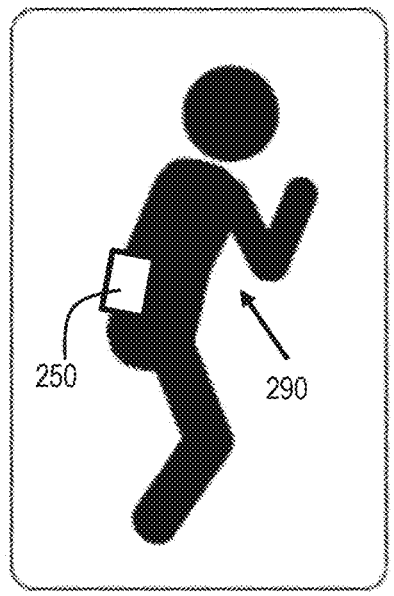
Figure 2D:
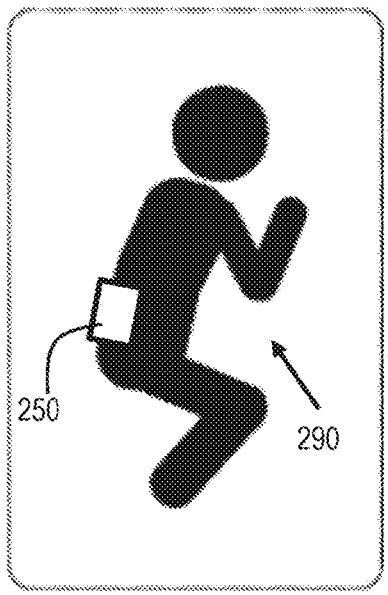
Figure 2E:
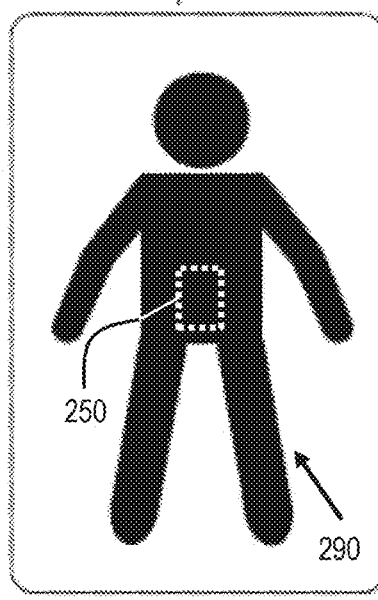

FIG. 2A through FIG. 2E are block diagrams that illustrate relationship of pressure sensors to patient posture, according to an embodiment. In this embodiment, an array of pressure sensors 250 is disposed along the surface of a patient 290 in the vicinity of the sacrum of the patient. Depending on the posture of the patient 290, the spatial distribution of pressure readings from the multiple pressure sensors in the pressure array 250 will vary. The direction of the array is deduced from the pressure variations along an x direction 251 and an, at least locally, perpendicular y direction 252 of the flat or curved array (called 2D and 2.5D arrays herein). In some embodiments, the posture of the patient is deduced from the spatial distribution of pressure readings. FIG. 2A depicts the disposition of the pressure array 250, and the x axis 251 and y axis 252, when the patient 290 is in a "Right Yearner" posture. FIG. 2B depicts the disposition of the pressure array 250 when the patient 290 is in a "Right Fetus" posture. FIG. 2C depicts the disposition of the pressure array 250 when the patient 290 is in a "Left Yearner" posture. FIG. 2D depicts the disposition of the pressure array 250 when the patient 290 is in a "Left Fetus" posture. FIG. 2E depicts the disposition of the pressure array 250, underneath the patient 290, when the patient 290 is in a "Supine" posture. In other embodiments, more or fewer postures are differentiated. In other embodiments the array 250 is configured to be attached to the patient at other portions of the patient different from the sacrum.

In some embodiments, determining posture or class of postures from spatial pressure variations can be done objectively and automatically by simply correlating the x and y directions of pressure variations with postures in the class, or using machine learning or other forms of artificial intelligence to learn the associated pressure variations and the posture classes using dozens to hundreds to thousands of examples in a training set, or some combination.

In some embodiments, a pressure plane is determined objectively and automatically in addition to, or instead of, a posture or class of postures, based on the spatial variations in pressure within the array. The determination of a pressure plane is described in more detail below in the examples section.

In various embodiments, a patient's susceptibility to, or risk of, or state of, pressure injury is based on a number of substantial movements made by the patient per unit time, either assisted or unassisted. In various embodiments, substantial movements are determined objectively and automatically based on posture changes or pressure plane changes that exceed some threshold change or some combination. In some embodiments, a pressure plane has a strength and a direction; and, changes in either or both are used objectively and automatically in the definition of a substantial movement. Examples of such objective and automatic determinations of substantial movements (or simply movements hereinafter) are described in more detail below with respect to an example embodiment.

Figure 3A:
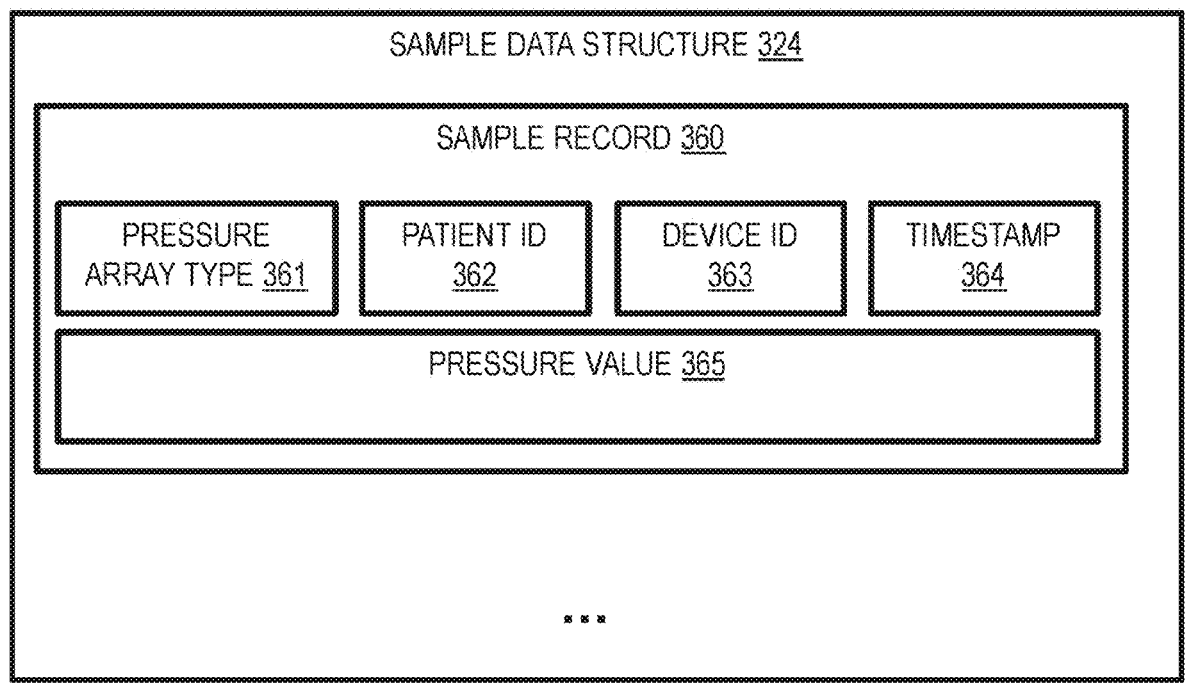
FIG. 3A and FIG. 3B are block diagrams that illustrate fields of data structures for the system of FIG. 1, according to an embodiment.
Figure 3B:
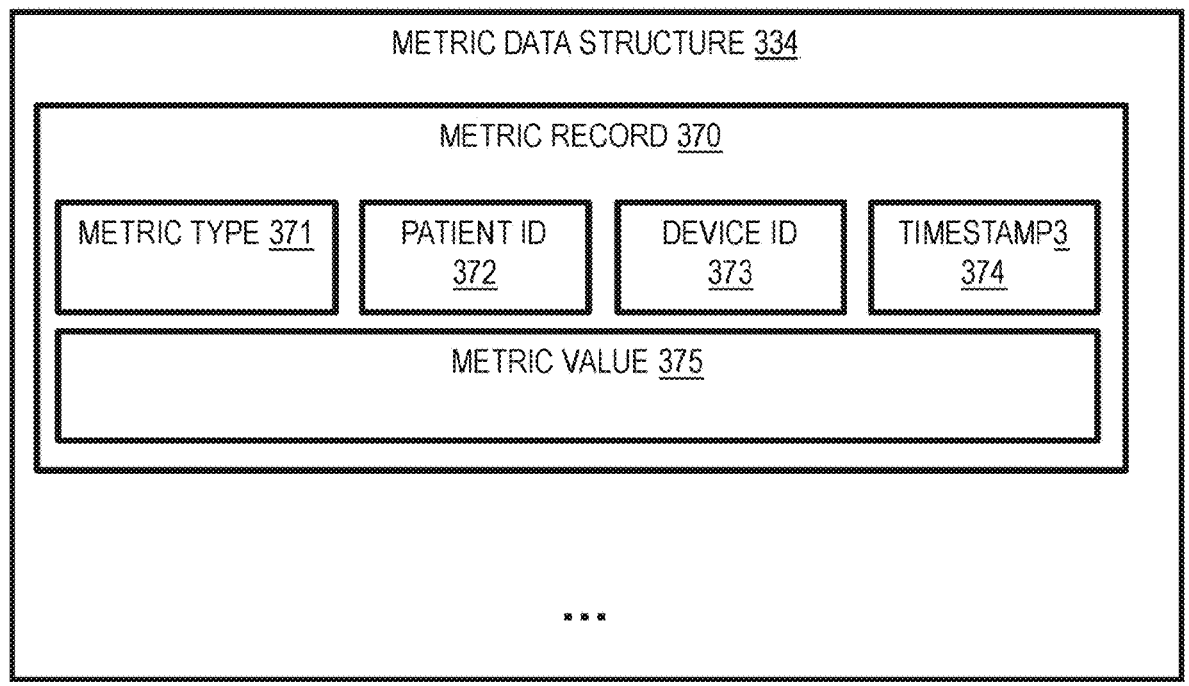

According to some embodiments, sample data is stored automatically in a data structure 124. In additions, one or more pressure change metrics or one or more movement metrics, or some combination, are objectively and automatically determined from the samples; and these metrics are stored in a data structure 134. FIG. 3A and FIG. 3B are block diagrams that illustrate fields of data structures 324 and 334 for the system of FIG. 1, according to an embodiment. FIG. 3A illustrates an example sample data structure 324, a particular embodiment of data structure 124. Each sample data structure 324 includes one or more sample records, including sample record 360 among other indicated by ellipsis. Each sample record includes a sample type field 361, a patient identifier (ID) field 362, a device identifier (ID) field 363, a timestamp field 364 and a sample value field 365.

The sample type field holds data that indicates a sample type, e.g., pressure readings. The patient ID field 362 holds data that uniquely indicates a particular patient under care of one or more care givers at a clinic or other facility. For privacy, the patient ID may be encrypted or associated with particulars about the patient in a separate secure or encrypted file. The device ID field 363 holds data that indicates a particular sensor (or array) that provides the sample type. The timestamp field 364 holds data that indicates a date and time that a sample was taken by the device indicated in the device ID field 363. The time resolution is suitable for the application, e.g., having a resolution that is a small fraction of the update period or real-time or low latency criterion, such as one tenth or one hundredth or one thousandth of the update period. The sample value field 365 holds data that indicates one or more values output by the pressure sensor or array indicated in device field 363 when measuring the physical state of the patient identified in patient ID field 362 associated with time indicated in the timestamp field 364. The number of values can be construed as one or more vectors, each with a same or different number of elements. For example, the sample value field holds a vector of 16 pressure values of the pressure array device indicated in device ID field 363 starting (or ending or centered) at a time given by timestamp 364 while attached to the patient indicated in the patient ID field 362. The number of vectors and the number of elements in each vector are associated in a sensor suite data structure, such as in data structure 142, with the sample type indicated in sample type field 361. In some embodiments, the sample value field 365 is single valued, equivalent to a single vector with a single element.

In various embodiments, the same fields are included in as fields in one or more data packets sent over a network. In some embodiments, one or more fields of record 360 or data packet hold encrypted data, so that patient data is securely stored or transmitted or both.

FIG. 3B illustrates an example metric data structure 334, a particular embodiment of metric data structure 134. Each metric data structure 334 includes one or more metric records, including metric record 370 among other indicated by ellipsis. Each metric record includes a metric type field 371, a patient identifier (ID) field 372, a device identifier (ID) field 373, a timestamp field 374, and a metric value field 375.

The metric type field holds data that indicates a metric derived from the sample type, e.g., a posture class or pressure plane direction or pressure plane strength. The patient ID field 372 holds data that uniquely indicates a particular patient under care of one or more care givers at a clinic or other facility, and often has the same contents as, or points to, field 362 in the sample data structure. The device ID field 373 holds data that indicates a particular sensor that provides the samples for the metric type, e.g., the pressure sensor array, and often has the same contents as, or points to, field 363 in the sample data structure. The timestamp field 374 holds data that indicates a date and time or time interval when one or more samples were taken by the device indicated in the device ID field 373 and used to derive the metric value. The time resolution is suitable for the application, e.g., having a resolution that is a small fraction of the update period or real-time or low latency criterion, such as one tenth or one hundredth or one thousandth of the update period. The metric value field 375 holds data that indicates one or more values output by the module 140 based on samples from the sensor indicated in device field 373 when measuring the condition of the patient identified in patient ID field 372 associated with time indicated in the timestamp field 374. The number of values can be construed as a number of vectors each with a same or different number of elements. The number of vectors and the number of elements in each vector are associated in a data structure, such as in data structure 142, with the metric type indicated in metric type field 371. In some embodiments, the sample value field 375 is single valued, equivalent to a single vector with a single element. For example, the metric value field holds single value indicating a number of movements in the previous ten minutes derived from the spatial distribution of pressure from the pressure array indicated in device ID field 373 starting (or ending or centered) at a time given by timestamp 374 while attached to the patient indicated in the patient ID field 372.

In various embodiments, the same fields are included as fields in one or more data packets sent over a network. In some embodiments, one or more fields of record 370 or data packet hold encrypted data, so that patient data is securely stored or transmitted or both.

Although fields, records and data structures are depicted in the FIG. 3A through FIG. 3B as integral blocks in a particular arrangement for purposes of illustration, in other embodiments one or more fields, records or data structures, or portions thereof, are arranged in a different manner, or are omitted, or one or more different fields or records or data structures are included.

1.2 PPIP Methods

Figure 4:
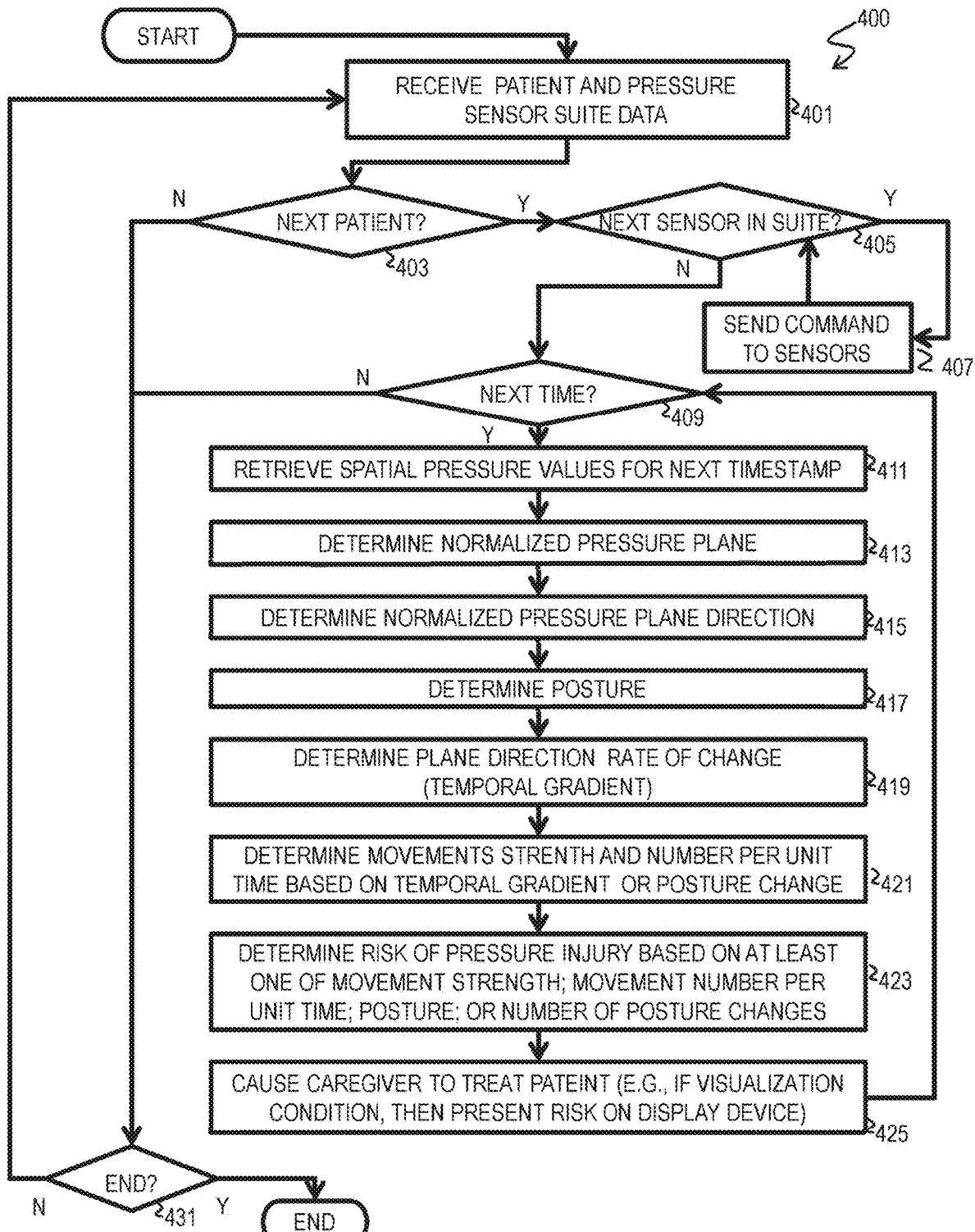
FIG. 4 is a flow chart that illustrates a method for patient pressure injury prevention, according to an embodiment.

FIG. 4 is a flow chart that illustrates a method for patient pressure injury prevention, according to an embodiment. Although steps are depicted in FIG. 4 as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways. These steps are performed by one or more PPIP modules 140, e.g., multiple modules 140 running in parallel in the same or in many different hosts or locations for one or more patients in one or more clinics or other facilities.

In step 401 patient and sensor suite data is received, either unsolicited or in response to a retrieval from or query to a local or remote database, such as from data structure 142. The sensor suite data indicates the device IDs, types of sensors, and patient ID for the sensing part of the system 100. This information is available for example in configuration type record or a configuration instance record on a local client or remote server module Also included is information about the native interactions with the sensors 150, including translations from commands into the native interaction with each of the sensors 150. Also included is information about how the sensor should be operated during the process, such as information about sampling rate and pressure range and sampling duration or end sampling conditions.

In step 403, it is determined whether there is a next patient for whom pressure injury is to be prevented. If not, control passes to step 431 to see if conditions are satisfied to end the process, such as no patients in the clinic or a system reboot. If such end conditions are satisfied, the process ends. Otherwise, control passes back to step 401 to get any updates on the sensors and patients for which the method is to be performed.

If it is determined in step 403 that there is a next patient, then control passes to step 405. In step 405, it is determined if there is another sensor in the suite for the current patient that should start measurements. If so, then, in step 407, one or more commands are issued to start the measurements. In some embodiments, the measurements are received in step 407 and control passes back to step 405 to determine if there is another sensor in the suite. In some embodiments, the entire array of pressure sensors is treated as a single sensor and operated with a single command. When there are no more sensors in the suite for the current patient, control passes to step 409.

In step 409, it is determined whether it is time to process another sample. In some embodiments, this occurs when a sample data packet is received from a sensor as a result of the commands sent in step 407. In some embodiments, one or more samples are received as data packets from sensors 150 and some or all are stored automatically in sample data structure 124 or 324. In these embodiments, step 409 determines when it is time to retrieve one or more samples from sample data structure 124 or 324. If it is determined in step 409 that it is not time to process another sample, control passes to step 431 to see if end conditions are satisfied, as described above.

If it is determined in step 409 that it is time to process another sample, control passes to step 411. In step 411, the samples of pressure measurements from the array of pressure sensors at the current one or more timestamps are retrieved, either as data packets from sensors, or from sample data structure 124 or 324. Thus, the method includes receiving, from a plurality of pressure sensors configured to be disposed in a spatial arrangement in contact with a patient, samples data that indicate pressure measurements by the plurality of sensors at each of a plurality of different times.

In step 413, a pressure plane is computed based on the pressure measurements form the pressure array. A pressure plane is defined in 3D space in which the first two dimensions are the spacing of pressure sensors in the x direction and y direction, respectively, and the third dimension is pressure. A plane is defined by three pressure sensors, so when the pressure array has more than three sensors, a best fit plane is determined through all the 3D space-pressure points, or two or more sensors are combined, such as by averaging to produce three average position-pressure points. For example, a particular averaging scheme is described below with reference to an example embodiment.

In some embodiments, the pressures are normalized by dividing each pressure by the maximum pressure observed during the observation of one patient, which corrects for the patient's weight among other factors. Thus, normalized pressures are between 0 and 1, inclusive.

The raw or normalized pressure plane has a direction perpendicular to the face of the plane and a magnitude based on the distance of the plane from a horizontal plane at zero pressure. The direction of the pressure plane is also called the "orientation of the patient" herein. Any method may be used to determine the magnitude (also called strength) of the pressure plane, such as the raw or normalized pressure at the midpoint of the plane above the array, or the instantaneous maximum raw or normalized pressure over the plane above the array, or some average of all the raw or normalized pressures contributing to the pressure plane. The pressure plane direction and strength are determined in step 415. In some embodiments, the pressure plane direction or strength or both are stored as metrics in metric data structure 134 or 334. Thus, the method includes determining at each of the plurality of different times an angular orientation of a patient based on the samples. In some embodiments, pressure planes are not used, and step 415 is omitted.

In step 417, a posture of the patient is determined. As used herein, the term "orientation of the patient" includes the posture of the patient. In some embodiments, the posture is determined by classifying each pressure plane magnitude and direction into one of several discrete postures, such as the five posture classes depicted in FIG. 2A through FIG. 2E, and determining which class the current patient's current pressure plane falls into. In some embodiments, the posture is based on the raw or normalized pressures of all the pressure sensors in the pressure array. In some embodiments, the pressure plane or pressure array measurements associated with each posture is learned, using a test or training set and machine learning. In some embodiments, the posture is stored as a metric in metric data structure 134 or 334. In some embodiments, posture is not used and step 417 is omitted.

In step 419, the temporal change in pressure plane is determined, called the temporal gradient, or simply gradient herein, at each time of interest. A temporal gradient can be determined for the pressure plane direction or the pressure plane strength or some combination. This is an example of determining a change in the angular orientation of the pressure at each successive time of the plurality of different times.

In step 421, movements are determined, where a movement is a significant change in patient pressure plane or posture. For example, in some embodiments a movement is a change in pressure plane direction (direction temporal gradient) that exceeds some angular threshold, or a pressure plane strength change (plane strength temporal gradient) that exceeds some strength threshold, or some combination. In some embodiments, a movement is a change in posture from one class of postures (e.g., right yearner) to another class of postures (e.g., supine). A change in posture class is another example of determining a change in the angular orientation of the pressure at each successive time of the plurality of different times. Step 421 includes characterizing the movement by strength of movement or rate of movement (e.g., the number of movements per unit time), or some combination. Thus, the method includes determining a value of a patient movement parameter based on the change in angular orientation of the patient. In some embodiments, the movement or movement strength or movement rate or some combination are stored as metrics in metric data structure 134 or 334.

In step 423, the patient's conditions is determined based on the movement strength or movement rate, or some combination. For example, the patient's risk of pressure injury or need for assisted movement, called herein a pressure injury category for the patient, is determined based on the history of movement strengths (e.g., cumulative strength) or movement rate (e.g., total number of movements) over the past number of hours. Thus, a pressure injury category for the patient is determined based on the value of the patient movement parameter. In some embodiments, the patient's risk or need for assisted movement or some combination is stored as one or more metrics in metric data structure 134 or 334.

In step 425, a caregiver provides treatment to the patient based on the patient's risk of pressure injury or need for assisted movement. For example, the patient's risk of pressure injury or need for assisted movement is presented as a time series over the past number of hours, or the time for the next assisted movement is presented. The presentation is on a display device configured to be visible to the caregiver. In response to the information presented, the caregiver goes to the patient and assists the patient in changing posture or otherwise moving, or the caregiver waits for a later time. Thus, the method includes presenting on a display device a pressure injury category for the patient based on the value of the patient movement parameter, wherein treatment of the patient by a caregiver is based on the pressure injury category.

After presenting results that can cause treatment in step 425, control passes to step 409 to determine if it is time to process the next samples, as described above.

2. Example Embodiments

Example embodiments of the system 100, are described here for an embodiment called pressure injury monitoring and prevention (PIMAP).

In the example embodiment, an objective way is presented to assess the pressure injury condition or risk of a patient in near real-time (e.g., at suitable low latency) using a novel wearable pressure-sensing device. This example embodiment uses a 4×4 array of pressure sensors configured to be disposed along the base of the patients' back, in the vicinity of the sacrum. Example methods are described on how to analyze the data to assess the mobility of the patient. The illustrated embodiment uses pressure plane direction temporal gradient above a threshold value as a movement. Example methods are also described on what analysis to perform to track the posture of the patient, and changes in posture, in addition to, or in lieu of, the pressure plane direction temporal gradient.

Figure 8A:
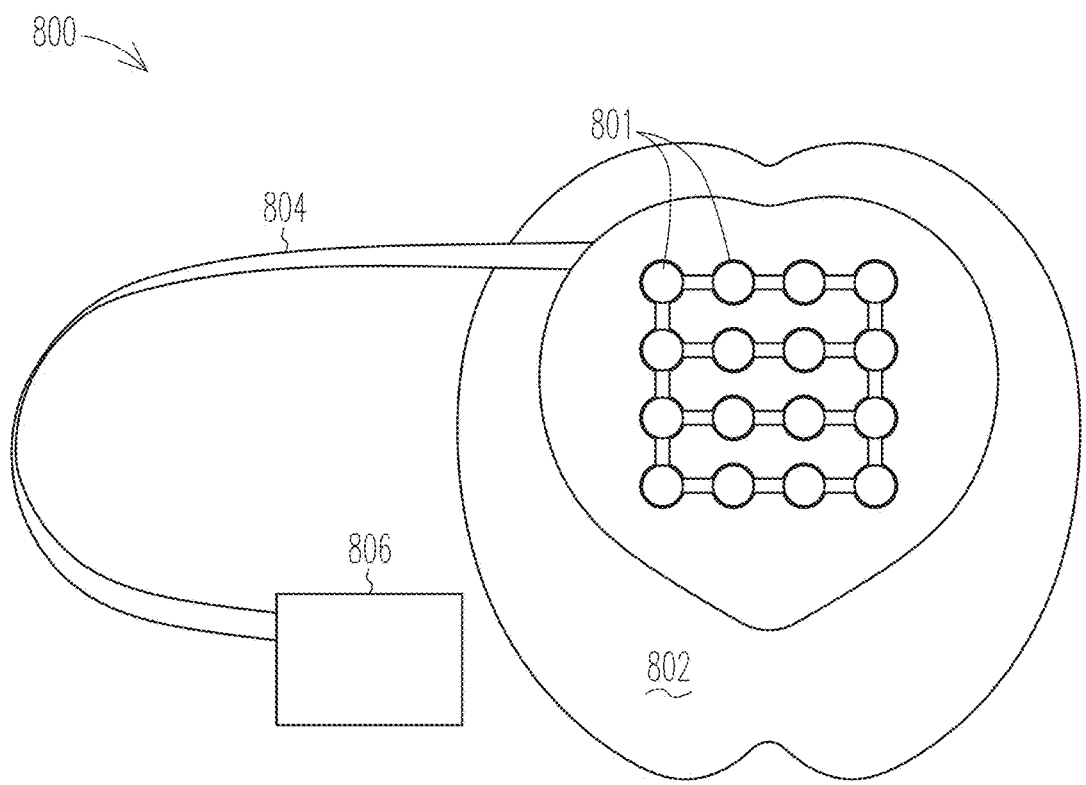
FIG. 8A is a photograph that illustrates an example of a sensor array configured to be disposed on a surface of a patient, according to an embodiment.

FIG. 8A is a photograph that illustrates an example of a sensor array assembly 800 configured to be disposed on a surface of a patient, according to an embodiment. The assembly 800 includes 16 pressure sensors 801 in a single dressing 802 that is configured to be included in a wrap to dispose the seniors against the skin of a patient, Each sensor 801 is connected by cable 804 terminating in a printed circuit board (PCB) within electronic box 806 for connection to a computer system or network.

Interface pressure was measured using a wearable pressure sensing array, such as assembly 800, placed between a MEPILEX BORDER SACRUM™ (Molnlycke Health Care, Gothenburg, Sweden) adhesive wound dressing and TEGADERM™ (3M, Maplewood, USA) transparent film dressing. The sensing array consisted of circular (1 cm diameter) flexible piezoresistive pressure sensors 801 (Micro Deformable Piezoresistive"UNEO™ sensors; Uneo Inc., New Taipei City, Taiwan) placed in a 4×4 array of sensors with 1 cm spacing between each sensor. These 16 cells were connected using 8 traces (4 vertical, 4 horizontal), which were routed through a 30 cm flexible cable 804 to PCB in box 806. The PCB consisted of a voltage divider circuit with fixed 10 kilo-ohm resistors in series with the variable pressure sensor resistors. The change in pressure sensors' resistance was measured using a microcontroller and Bluetooth transmitter/receiver chip (BLE 112 module; Silicon Labs, Austin, USA), which scanned and transmitted (frequency=1 Hertz) the measurements to an IPAD MINI 2™ (Apple Inc. Cupertino, USA) running an application programmed as PPIP module 140.

There were a total of five patients included in this example embodiment. A criteria for enrollment in the study was a score of 1 for activity, mobility, and friction/sheer on the Braden Scale. The patient's skin was observed for lesions, baseline documentation was performed, and the pressure sensitive wound dressing was placed on the sacrum of the patient following standard Mepilex application procedures. The end of the flexible flat cable 804 was plugged into the electronics box 806 and a coin cell battery was placed into the electronics box 806. The PPIP module 140 was selected on the iPad and the patient's study number was entered into the application. Once the patient's number was entered into the application, the iPad was connected to the BLE112 and commenced data collection. Data was collected until the dressing was changed (during which data was not collected, but after which data collection resumed), the patient left the ICU (Intensive Care Unit), or the patient was disenrolled from the study comprising this embodiment.

Figure 8B:
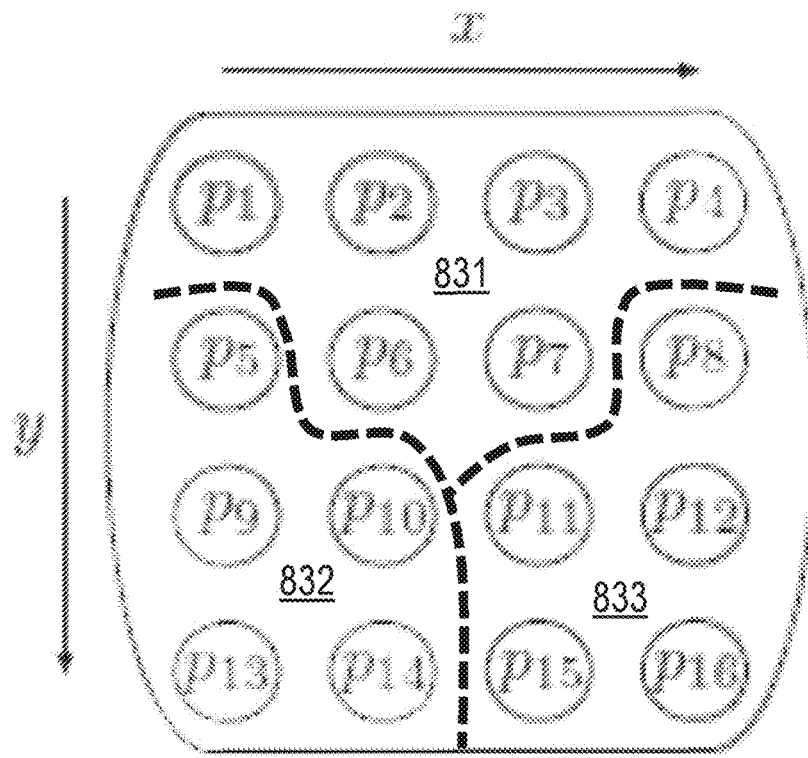
FIG. 8B is a block diagram that illustrates an example of a spatial arrangement of pressure sensors configured to be disposed on a surface of a patient in a vicinity of the patient's sacrum, according to an embodiment.
Figure 9A:
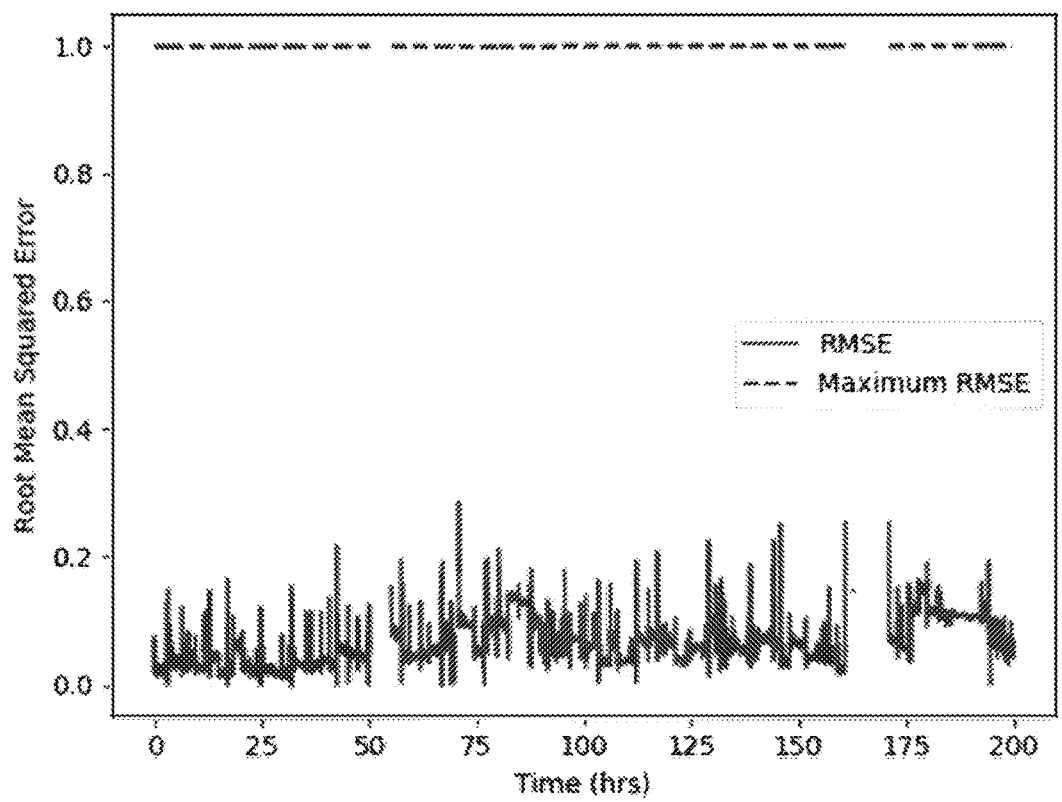
FIG. 9A through 9E are plots that illustrate example measurements of pressure deviation from a best-fit pressure plane, as measured for each of five patients, respectively, according to an embodiment.
Figure 9B:
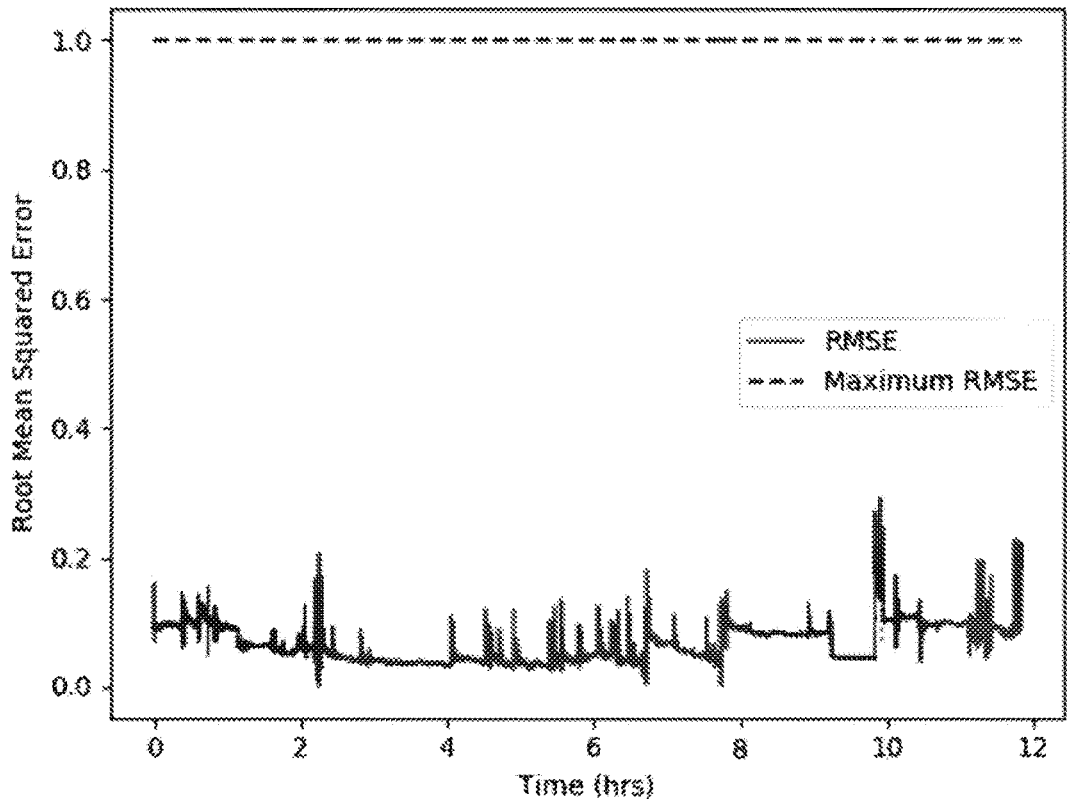
Figure 9C:
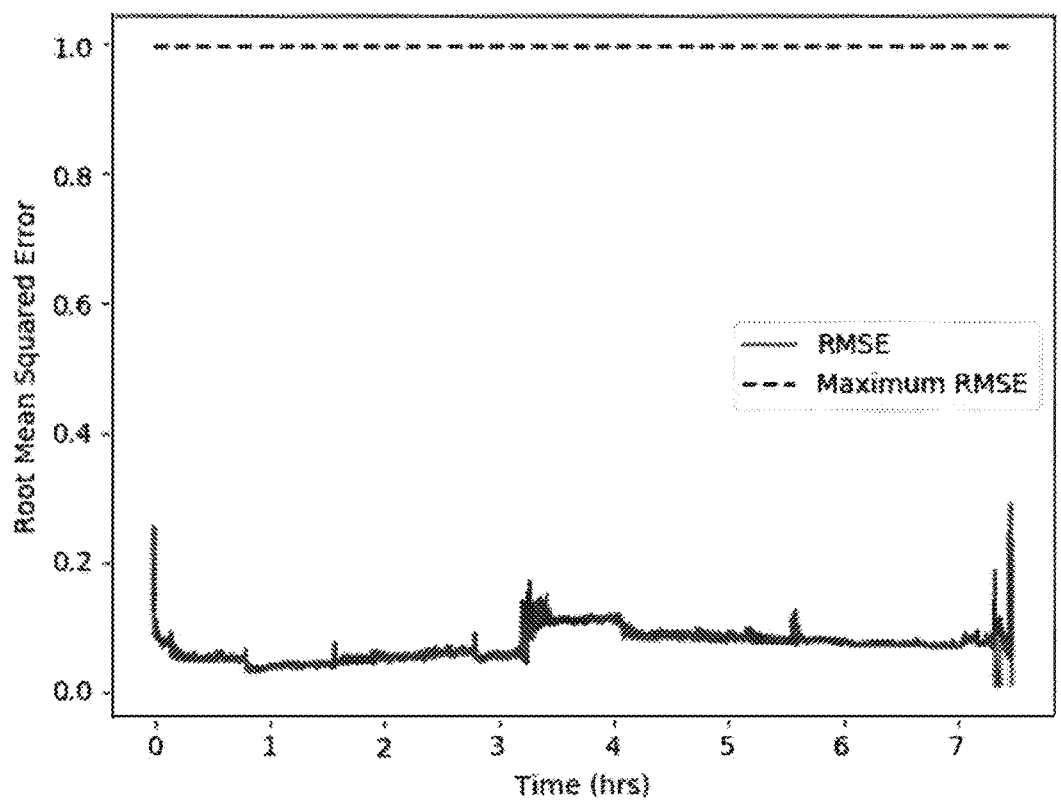
Figure 9D:
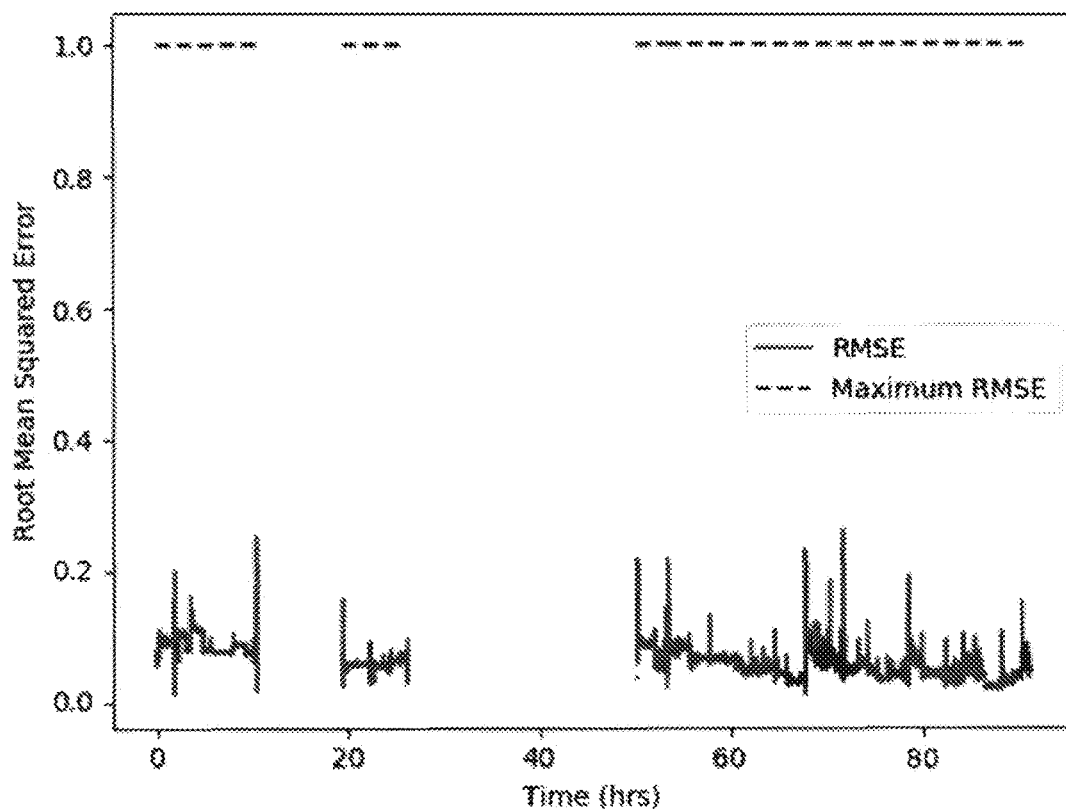
Figure 9E:
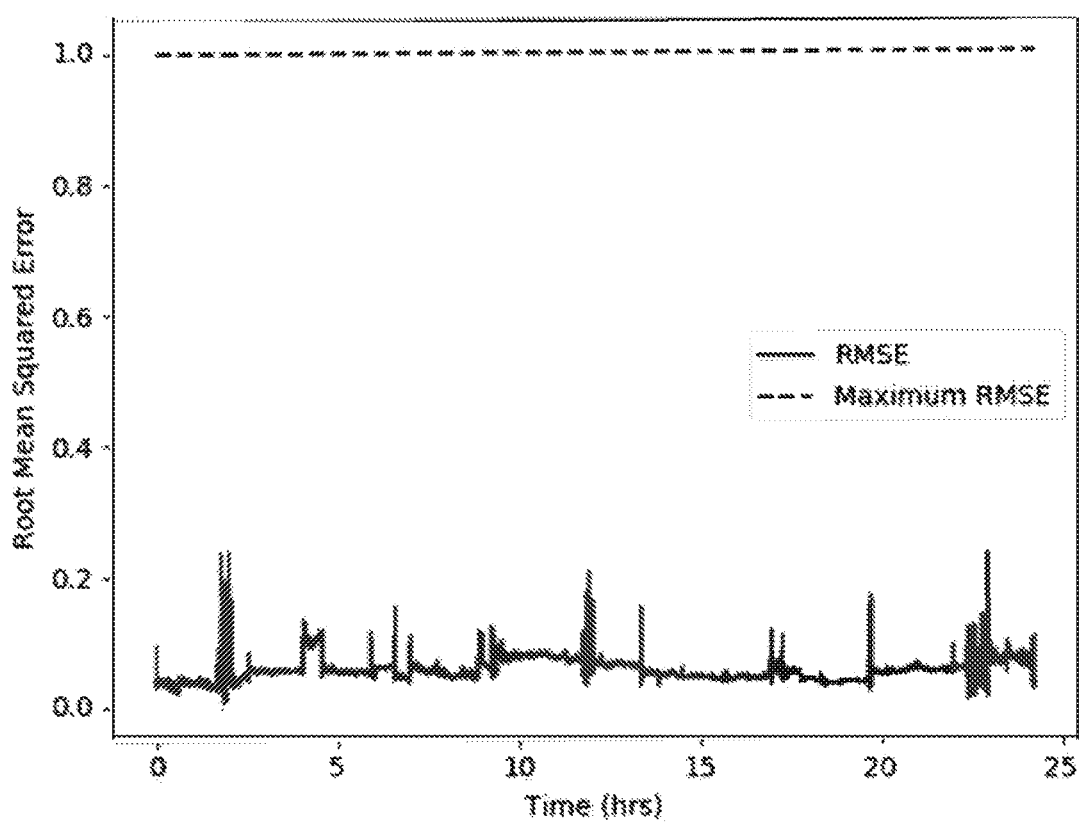

At every reading of the sensor array, one pressure reading from each pressure location for a total of sixteen pressure readings were obtained, where the relative position of each pressure location is known as depicted in FIG. 8B. FIG. 8B is a block diagram that illustrates an example of a spatial arrangement of pressure sensors configured to be disposed on a surface of a patient in a vicinity of the patient's sacrum, according to an embodiment. The 16 pressure sensors are labeled $p_1$ through $p_{16}$ and arranged in four rows, each oriented in an x-direction, and four columns, each oriented in a y direction. Our goal is to interpret this data to infer the mobility and posture of the patient. We form a best-fit linear plane to the sensors pressure readings and then use the planar characteristics to infer movement and posture.

For the purpose of the description herein, a cell was defined as a triplet with the three values x; y; p, where x is the horizontal position within the array, y is the vertical position within the array, and p is the pressure reading at that x; y position. An x,y location was assigned at each cell and the three values x,y,p were normalized. x and y were normalized on assignment such that the highest value of x and y is 1. The pressure values were normalized such that the maximum possible pressure value is 1. Hereinafter, the values of the variables x,y, p are the normalized values. As an example, the four corner cells have values given by Equations 1a through 1d.

$$\text{cell1}=(0;0;p1); \quad (1a)$$

$$\text{cell4}=(1;0;p4); \quad (1b)$$

$$\text{cell13}=(0;1;p13); \quad (1c)$$

$$\text{cell16}=(1;1;p16). \quad (1d)$$

Given any three triplets, one can form a plane. In some embodiments, readings from several sensors were averaged together. In the example embodiment, the sensor readings were averaged within each of three cell groupings, each called a groupcell. The groupcells are divided by dashed lines in FIG. 8B and labeled groupcell1 (831), groupcell2 (832), and groupcell3 (833). The definition of the groupcells is given by Equations 2a through 2c., $$\text{groupcell1}=\text{average}(\text{cell1};\text{cell2};\text{cell3};\text{cell4};\text{cell6};\text{cell7}) \quad (2a)$$

$$\text{groupcell2}=\text{average}(\text{cell5};\text{cell9};\text{cell10};\text{cell13};\text{cell14}) \quad (2b)$$

$$\text{groupcell3}=\text{average}(\text{cell8};\text{cell11};\text{cell12};\text{cell15};\text{cell16}) \quad (2c)$$

The averaging of the cells helps to form a best-fit plane; and, in addition it helps to eliminate some of the noise affecting the pressure sensors.

From the groupcells, one can form a plane pressure d by finding the normal vector n to the plane defined by the three groupcells (where pressure is the third dimension in this space) by performing the cross product of two vectors in the plane, e.g., vectors connecting one groupcell to each of the other two groupcells. Using the normal vector n and a point on the plane, e.g., one of the groupcells, one can then solve for the final value in the planar equation. A calculation to find the complete planar equation using threecells is given by equations 3a through 3d.

$$v12=\text{groupcell2}-\text{groupcell1} \quad (3a)$$

$$v13=\text{groupcell3}-\text{threecell1} \quad (3b)$$

$$n=v12\times v13 \quad (3c)$$

$$d=\text{groupcell1}n^T=ax+by+c \quad (3d)$$

From this best fit pressure plane d based on all 16 pressure sensors, two characteristics, the xslope and yslope can be used to describe the pressure distribution and relate that distribution to position of the patient. Although one could use the xslope and yslope directly for objective mobility and posture analysis, instead new metrics are used which are related to the xslope and yslope, and which are called the xangle or yangle, or some combination. These are defined as given by Equations 4a through 4d.

$$x\text{slope}=-a/c \quad (4a)$$

$$y\text{slope}=-b/c \quad (4b)$$

$$x\text{angle}=\arctan(x\text{slope})*360/2\pi \quad (4c)$$

$$y\text{angle}=\arctan(y\text{slope})*360/2\pi \quad (4d)$$

The xangle and yangle give a more intuitive way to think about the rotation of the patient, although it is important to keep in mind that the degrees values of these metrics are not actual degrees of rotation the patient is experiencing, but instead are used as relative metrics.

This best-fit plane is verified by calculating the Root Mean Squared Error of the actual 16 pressure values from the best-fit plane. FIG. 9A through 9E are plots that illustrate example measurements of pressure deviation from a best-fit pressure plane, as measured for each of five patients, respectively, according to an embodiment. In each plot, the horizontal axis indicates time in hours. Note that the plots have different duration for different patients. In each plot, the vertical axis indicates root mean square error (RMSE) of measured pressure from the best-fit pressure plane. The RMSE values are normalized to a maximum RMSE for the patient at 1.0. Each experiment lasted for a different amount of time and therefore the graph time scales are not equivalent. Also, a gap in data means the sensor was disconnected for that period of time. It can be seen that the best-fit plane is close to the actual values. It is noted that one does not expect the RMSE to be zero as the sensor information is being approximated as a linear plane. This simplification may not always be accurate as current pressure values may be better modelled as a quadratic, exponential, logarithmic, or other curved surface. In addition, the process of forming the best-fit linear plane eliminates noise, which also contributes to RMSE. Overall the RMSE is mostly below 0.2, which is acceptable.

Next, in this embodiment, an objective mobility metric is defined based on the sensor readings. The term mobility is used herein as defined in the Braden Scale—the patient's ability to change body position. The mobility score can have one of four values. A one, "completely immobile", indicates the patient cannot change body position without assistance. A two, "very limited", indicates the patient can make slight changes that are not frequent or significant. A three, "slightly limited", indicates the patient can make frequent small movements. A four, "no limitations", indicates the patient can make significant changes frequently and independently. Garcia-Fernandez et al conducted a study to determine the top risk dimensions that cause pressure injuries from an expert panel. The expert panel determined that mobility is in the top five risk dimensions that lead to pressure injuries. In addition, Alderden et al. surveyed the literature and also identified mobility as one of the top five risk factors for pressure injuries.

In this example embodiment, two metrics are developed to assess mobility: movements per minute, Movements/min, and movement strength, MovementStrength. Both metrics are based on the following definition of a movement. A movement is calculated by setting a threshold on both the x and y angle temporal gradients. the gradient at i, is calculated where i is the ith sample. For this example embodiment, the cells are sampled at every second and therefore i corresponds to the number of seconds. The gradient is calculated based on the xangle and yangle as seen in Equations 5a and 5b.

$$x\text{gradient}(i) = \begin{cases} x\text{angle}(i+1) - x\text{angle}(i) & \text{if } i = 0 \\ x\text{angle}(i) - x\text{angle}(i-1) & \text{if } i = \text{last value} \\ \dfrac{x\text{angle}(i+1) - x\text{angle}(i-1)}{2} & \text{otherwise} \end{cases} \quad (5a)$$

$$ygradient(i) = \begin{cases} yangle(i+1) - yangle(i) & \text{if } i = 0 \\ yangle(i) - yangle(i-1) & \text{if } i = \text{last value} \\ \dfrac{yangle(i+1) - yangle(i-1)}{2} & \text{otherwise} \end{cases} \quad (5b)$$

The xgradient and ygradient are then combined into a singular xygradient metric that does not differentiate between positive and negative angle, as given by Equation 6a.

$$xygradient(i) = \max(|xgradient(i)|, |ygradient(i)|) \quad (6a)$$

The xygradient is considered an objective mobility metric. A movement was defined as an xygradient value above a threshold, defined as xygradient(i)>2 based on visual inspection of the data. This definition of movement is given in Equation 6b.

$$\text{Movement} = \begin{cases} \text{True} & \text{if } xygradient > 2 \\ \text{False} & \text{otherwise} \end{cases} \quad (6b)$$

The metric Movements/min is the number of entries in xygradient that have a value larger than 2 (i.e., the number of Movements) divided by the number of minutes that have elapsed. MovementStrength is the average of the xygradient values that are greater than 2.

Figure 10A:
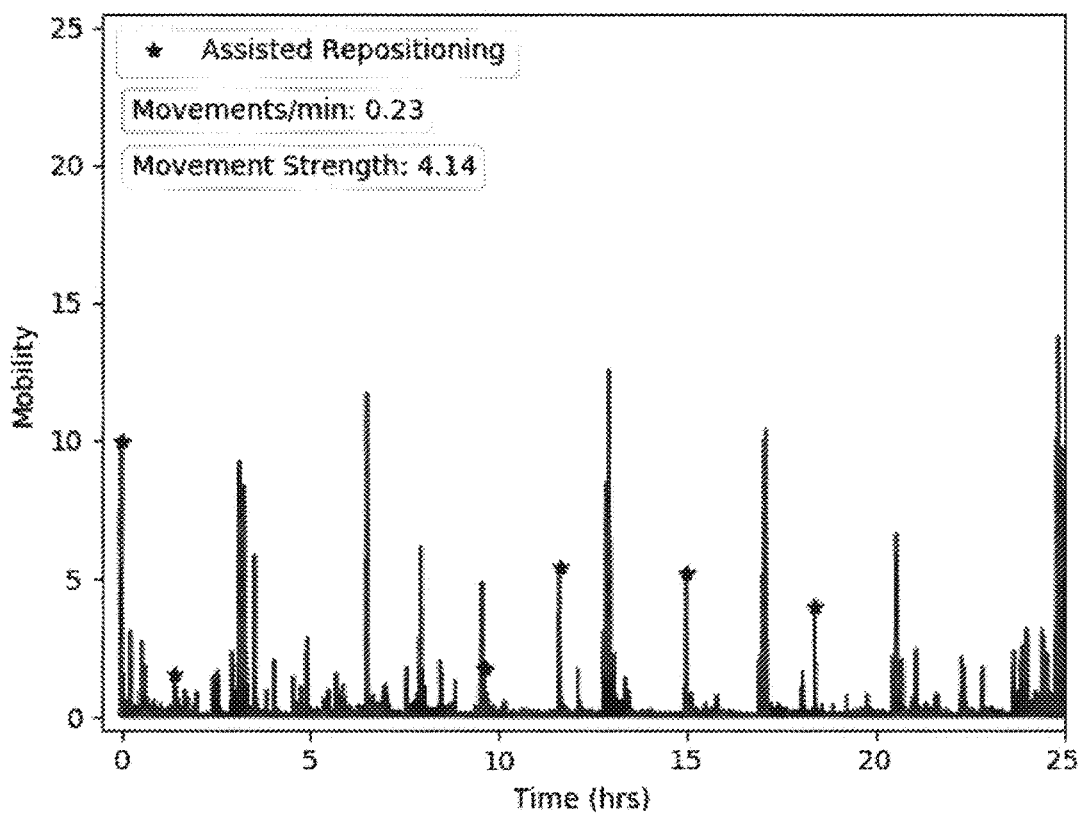
FIG. 10A through FIG. 10E are plots that illustrate example time series of objective mobility for the same five patients, respectively, according to an embodiment.
Figure 10B:
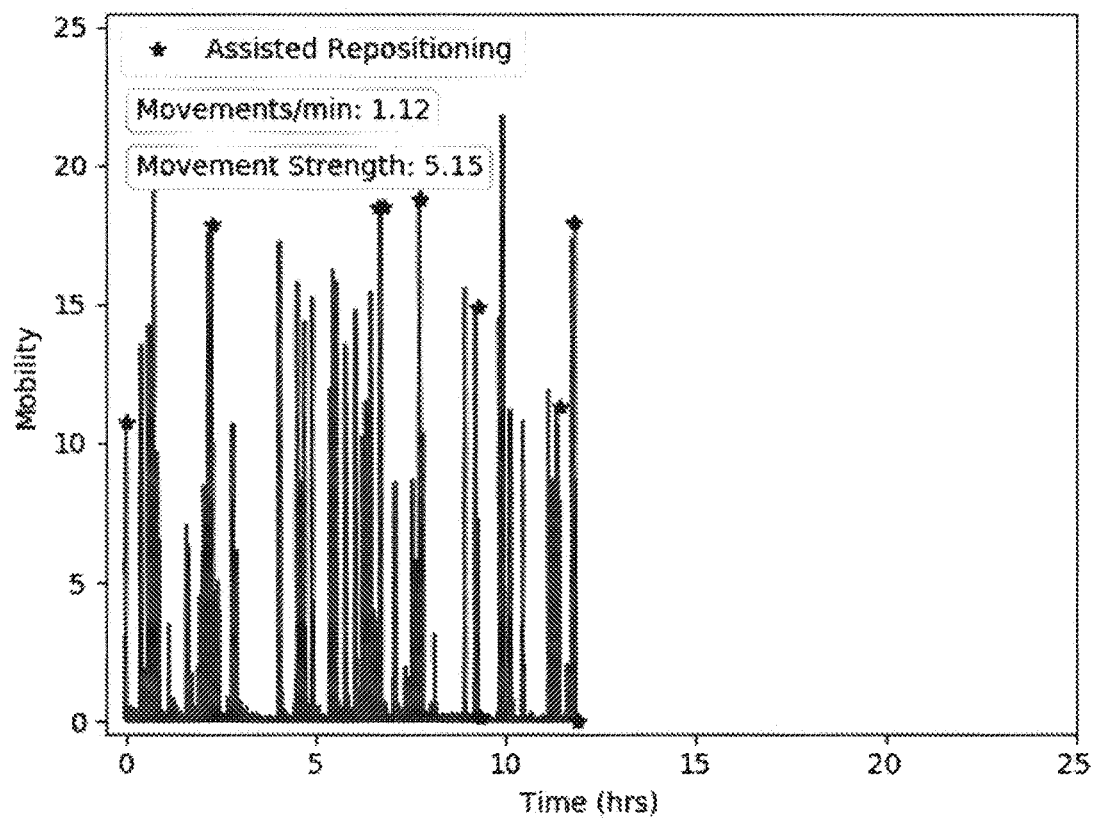
Figure 10C:
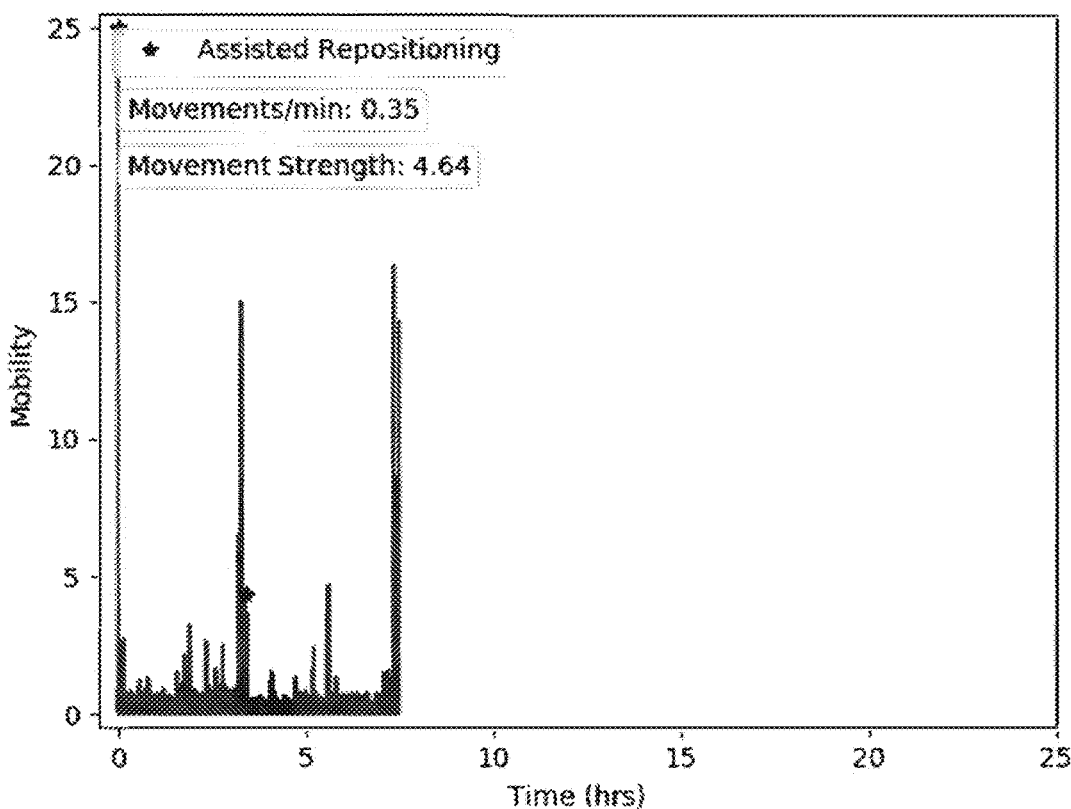
Figure 10D:
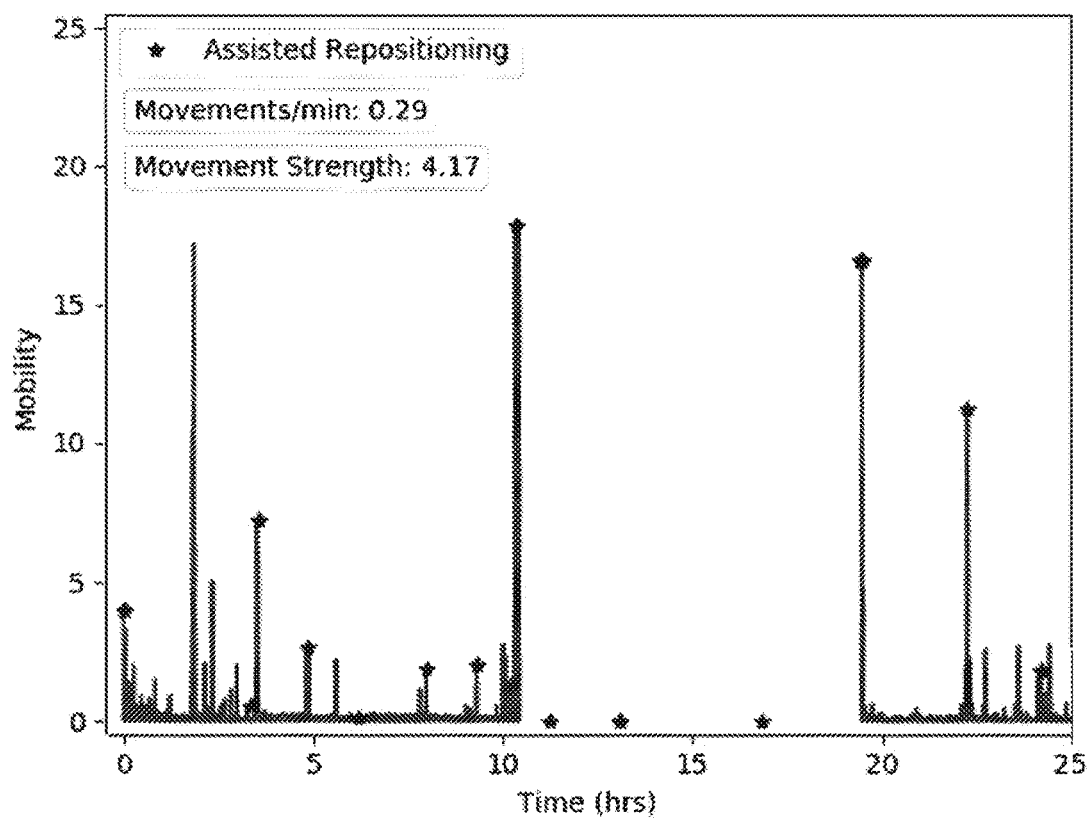
Figure 10E:
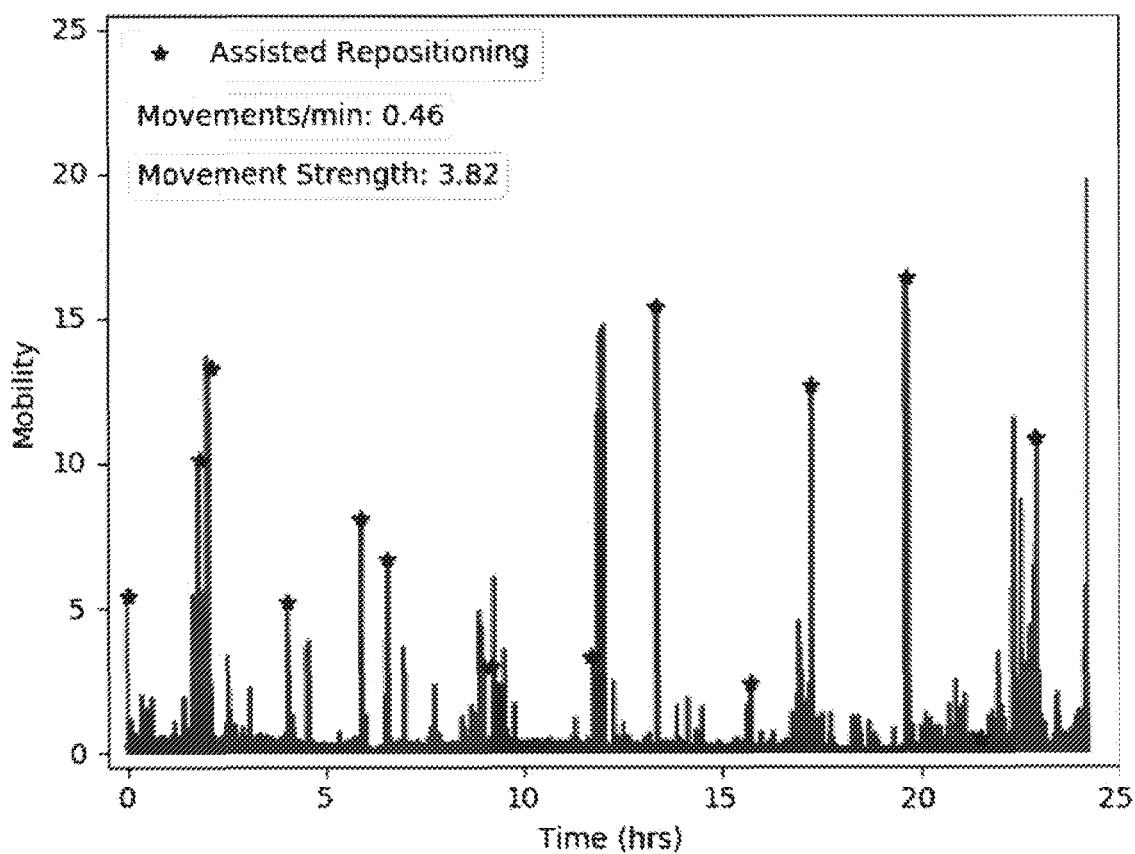

FIG. 10A through FIG. 10B are plots that illustrate example time series of objective mobility for the same five patients as depicted in FIG. 9A through FIG. 9E, respectively, according to an embodiment. In each plot, the horizontal axis indicates time in hours. Note that every plot has a horizontal axis with the same extent of 25 hours. The length of each experiment varied, but for comparison only the first 24 hours of each experiment are depicted. For certain segments of time no data is displayed, e.g. patient 2, patient 3, patient 4. This is either because the experiment was shorter than 24 hours or the pressure-sensing device was disconnected for a certain amount of time. In each plot, the vertical axis indicates objective mobility (i.e., xygradient in this embodiment). Note that every plot has a vertical axis with the same extent of 25 Movements/min. Below the legend in each graph are listed the calculated metrics Movements/min and MovementStrength. On each mobility graph, marked with a solid star, are times when the patient was repositioned by healthcare staff. This gives a sense of which movements were made by the patient and which were assisted. It is easy to see visually how a higher Movements/min corresponds to more frequent movements by the patient. Although data is plotted for only 24 hours for comparison, the objective metrics Movements/min and MovementStrength are calculated based on the entire length of the experiment and only when the sensing 800 device is connected.

The posture of the patient is tracked using the xangle and yangle from Equations 4c and 4d. Data from a short experiment of a healthy volunteer that includes reliable labels of posture was used. Movement were first filtered out based on the definition from Equation 6b. That is, intervals when xygradient were greater than 2 were not used for posture determination. The values of xangle and yangle were then plotted against the labels.

Figure 11:
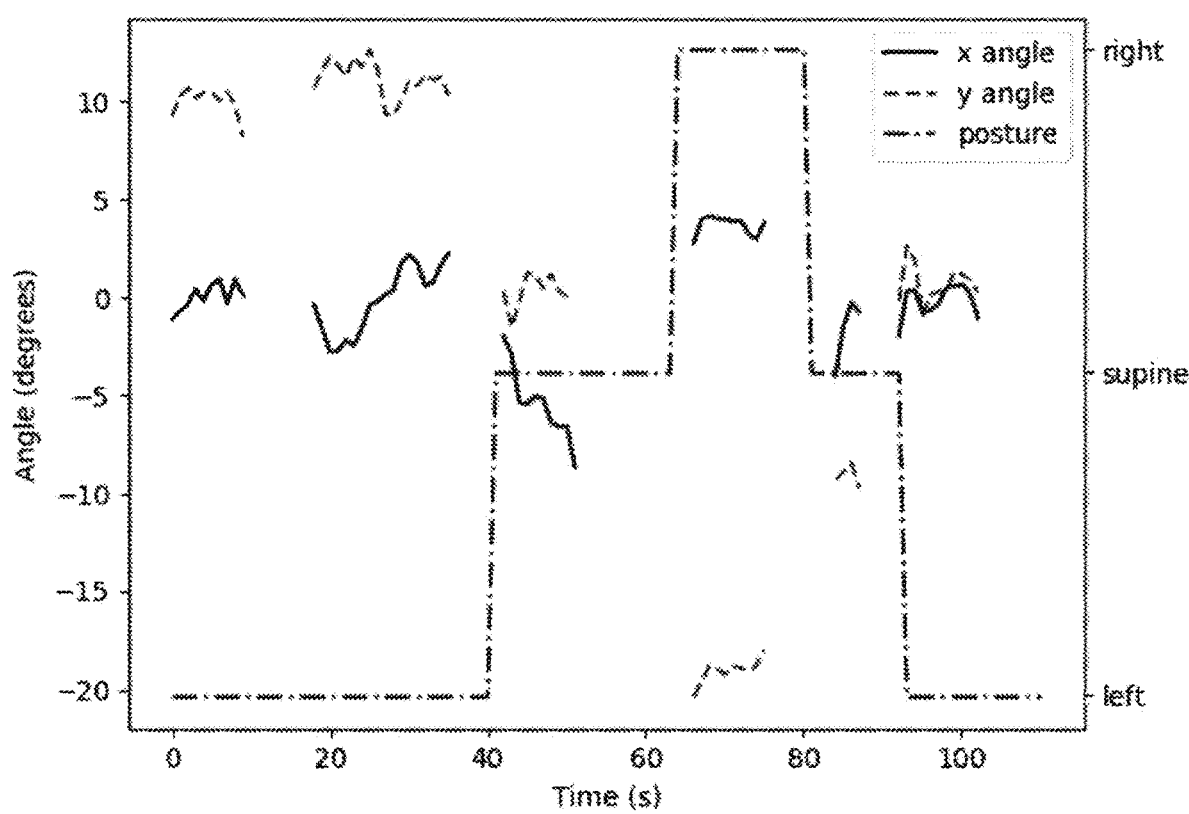
FIG. 11 is a plot that illustrates example measured values of x angle and y angle of a pressure plane and inferred patient posture, according to an embodiment.

FIG. 11 is a plot that illustrates example measured values of x angle and y angle of a pressure plane and inferred patient posture, according to an embodiment. The horizontal axis indicates time in seconds, from 0 to about 110. The left vertical axis indicates angle in degrees for xangle and yangle, and the right vertical axis indicates one of three postures, left bend (e.g., left yearner or left fetus), supine, and right bend (right yearner or right fetus). The solid trace indicates xangle, the dashed trace indicates yangle, both using the left-side vertical axis; and the dot-dash trace indicates posture using the right-side vertical axis.

The xangle and yangle have a value of 0 when there is an equal amount of pressure across the sensor device. This means, in theory, regardless of posture, the xangle and yangle can be 0. From the data of this embodiment, it was often found that there is a pressure slope across the sensor and it was attempted to use this to infer the posture of the patient. The intuitive expectation based on the orientation of the sensor is that when xangle value is negative the patient is on their left side, and when xangle value is positive the patient is on their right side. When the patient is supine, one would expect an xangle value close to 0. Likewise, the yangle should correspond to the amount of elevation the patient's head is above the patient's back. Using data such as that depicted in FIG. 11 a relationship between xangle/yangle and posture is expected. In some embodiments, the relationship is further refined using a Machine Learning or Artificial Intelligence (ML/AI) approach.

3. Computational Hardware Overview

Figure 5:
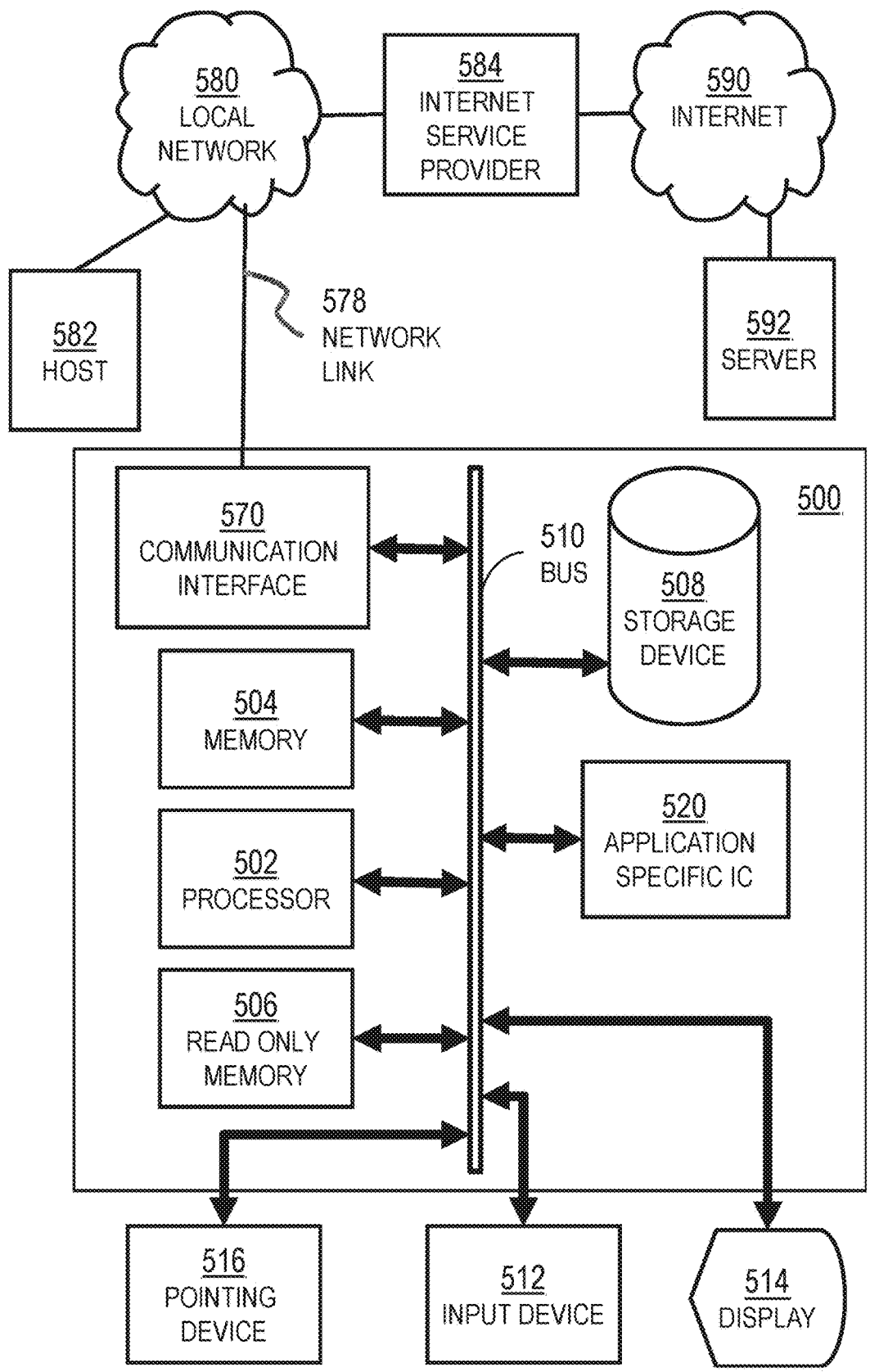
FIG. 5 is a block diagram that illustrates a computer system upon which an embodiment of the invention may be implemented.

FIG. 5 is a block diagram that illustrates a computer system 500 upon which an embodiment of the invention may be implemented. Computer system 500 includes a communication mechanism such as a bus 510 for passing information between other internal and external components of the computer system 500. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 500, or a portion thereof, constitutes a means for performing one or more steps of one or more methods described herein.

A sequence of binary digits constitutes digital data that is used to represent a number or code for a character. A bus 510 includes many parallel conductors of information so that information is transferred quickly among devices coupled to the bus 510. One or more processors 502 for processing information are coupled with the bus 510. A processor 502 performs a set of operations on information. The set of operations include bringing information in from the bus 510 and placing information on the bus 510. The set of operations also typically include comparing two or more units of information, shifting positions of units of information, and combining two or more units of information, such as by addition or multiplication. A sequence of operations to be executed by the processor 502 constitutes computer instructions.

Computer system 500 also includes a memory 504 coupled to bus 510. The memory 504, such as a random access memory (RAM) or other dynamic storage device, stores information including computer instructions. Dynamic memory allows information stored therein to be changed by the computer system 500. RAM allows a unit of information stored at a location called a memory address to be stored and retrieved independently of information at neighboring addresses. The memory 504 is also used by the processor 502 to store temporary values during execution of computer instructions. The computer system 500 also includes a read only memory (ROM) 506 or other static storage device coupled to the bus 510 for storing static information, including instructions, that is not changed by the computer system 500. Also coupled to bus 510 is a non-volatile (persistent) storage device 508, such as a magnetic disk or optical disk, for storing information, including instructions, that persists even when the computer system 500 is turned off or otherwise loses power.

Information, including instructions, is provided to the bus 510 for use by the processor from an external input device 512, such as a keyboard containing alphanumeric keys operated by a human user, or a sensor. A sensor detects conditions in its vicinity and transforms those detections into signals compatible with the signals used to represent information in computer system 500. Other external devices coupled to bus 510, used primarily for interacting with humans, include a display device 514, such as a cathode ray tube (CRT) or a liquid crystal display (LCD), for presenting images, and a pointing device 516, such as a mouse or a trackball or cursor direction keys, for controlling a position of a small cursor image presented on the display 514 and issuing commands associated with graphical elements presented on the display 514.

In the illustrated embodiment, special purpose hardware, such as an application specific integrated circuit (IC) 520, is coupled to bus 510. The special purpose hardware is configured to perform operations not performed by processor 502 quickly enough for special purposes. Examples of application specific ICs include graphics accelerator cards for generating images for display 514, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 500 also includes one or more instances of a communications interface 570 coupled to bus 510. Communication interface 570 provides a two-way communication coupling to a variety of external devices that operate with their own processors, such as printers, scanners and external disks. In general, the coupling is with a network link 578 that is connected to a local network 580 to which a variety of external devices with their own processors are connected. For example, communication interface 570 may be a parallel port or a serial port or a universal serial bus (USB) port on a personal computer. In some embodiments, communications interface 570 is an integrated services digital network (ISDN) card or a digital subscriber line (DSL) card or a telephone modem that provides an information communication connection to a corresponding type of telephone line. In some embodiments, a communication interface 570 is a cable modem that converts signals on bus 510 into signals for a communication connection over a coaxial cable or into optical signals for a communication connection over a fiber optic cable. As another example, communications interface 570 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 570 sends and receives electrical, acoustic or electromagnetic signals, including infrared and optical signals, that carry information streams, such as digital data.

The term computer-readable medium is used herein to refer to any medium that participates in providing information to processor 502, including instructions for execution. Such a medium may take many forms, including, but not limited to, non-volatile media, volatile media and transmission media. Non-volatile media include, for example, optical or magnetic disks, such as storage device 508. Volatile media include, for example, dynamic memory 504. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 502, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 502, except for carrier waves and other signals.

Logic encoded in one or more tangible media includes one or both of processor instructions on a computer-readable storage media and special purpose hardware, such as ASIC 520.

Network link 578 typically provides information communication through one or more networks to other devices that use or process the information. For example, network link 578 may provide a connection through local network 580 to a host computer 582 or to equipment 584 operated by an Internet Service Provider (ISP). ISP equipment 584 in turn provides data communication services through the public, world-wide packet-switching communication network of networks now commonly referred to as the Internet 590. A computer called a server 592 connected to the Internet provides a service in response to information received over the Internet. For example, server 592 provides information representing video data for presentation at display 514.

The invention is related to the use of computer system 500 for implementing the techniques described herein. According to one embodiment of the invention, those techniques are performed by computer system 500 in response to processor 502 executing one or more sequences of one or more instructions contained in memory 504. Such instructions, also called software and program code, may be read into memory 504 from another computer-readable medium such as storage device 508. Execution of the sequences of instructions contained in memory 504 causes processor 502 to perform the method steps described herein. In alternative embodiments, hardware, such as application specific integrated circuit 520, may be used in place of or in combination with software to implement the invention. Thus, embodiments of the invention are not limited to any specific combination of hardware and software.

The signals transmitted over network link 578 and other networks through communications interface 570, carry information to and from computer system 500. Computer system 500 can send and receive information, including program code, through the networks 580, 590 among others, through network link 578 and communications interface 570. In an example using the Internet 590, a server 592 transmits program code for a particular application, requested by a message sent from computer 500, through Internet 590, ISP equipment 584, local network 580 and communications interface 570. The received code may be executed by processor 502 as it is received, or may be stored in storage device 508 or other non-volatile storage for later execution, or both. In this manner, computer system 500 may obtain application program code in the form of a signal on a carrier wave.

Various forms of computer readable media may be involved in carrying one or more sequence of instructions or data or both to processor 502 for execution. For example, instructions and data may initially be carried on a magnetic disk of a remote computer such as host 582. The remote computer loads the instructions and data into its dynamic memory and sends the instructions and data over a telephone line using a modem. A modem local to the computer system 500 receives the instructions and data on a telephone line and uses an infra-red transmitter to convert the instructions and data to a signal on an infra-red a carrier wave serving as the network link 578. An infrared detector serving as communications interface 570 receives the instructions and data carried in the infrared signal and places information representing the instructions and data onto bus 510. Bus 510 carries the information to memory 504 from which processor 502 retrieves and executes the instructions using some of the data sent with the instructions. The instructions and data received in memory 504 may optionally be stored on storage device 508, either before or after execution by the processor 502.

Figure 6:
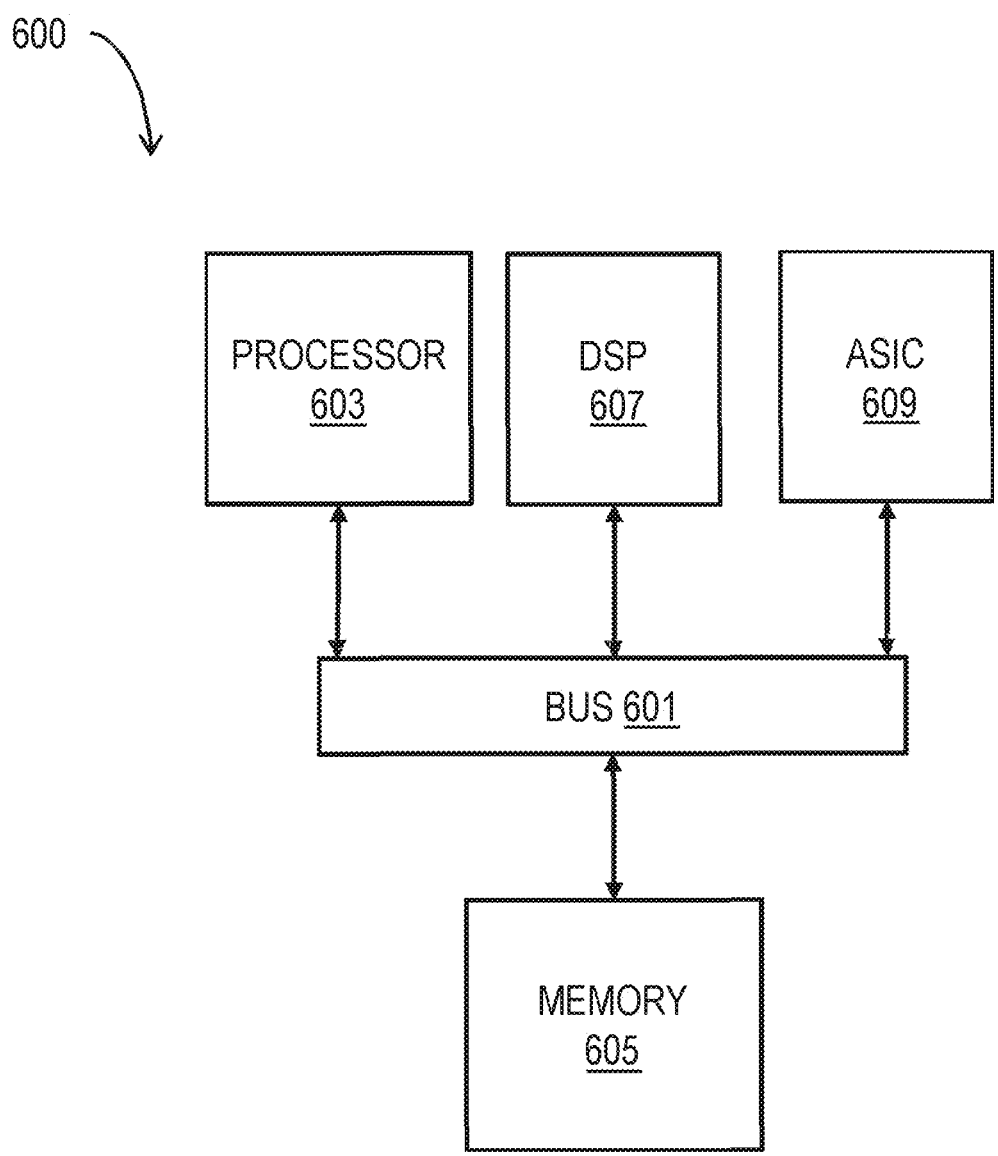
FIG. 6 illustrates a chip set upon which an embodiment of the invention may be implemented.

FIG. 6 illustrates a chip set 600 upon which an embodiment of the invention may be implemented. Chip set 600 is programmed to perform one or more steps of a method described herein and includes, for instance, the processor and memory components described with respect to FIG. 5 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 600, or a portion thereof, constitutes a means for performing one or more steps of a method described herein.

In one embodiment, the chip set 600 includes a communication mechanism such as a bus 601 for passing information among the components of the chip set 600. A processor 603 has connectivity to the bus 601 to execute instructions and process information stored in, for example, a memory 605. The processor 603 may include one or more processing cores with each core configured to perform independently. A multi-core processor enables multiprocessing within a single physical package. Examples of a multi-core processor include two, four, eight, or greater numbers of processing cores. Alternatively or in addition, the processor 603 may include one or more microprocessors configured in tandem via the bus 601 to enable independent execution of instructions, pipelining, and multithreading. The processor 603 may also be accompanied with one or more specialized components to perform certain processing functions and tasks such as one or more digital signal processors (DSP) 607, or one or more application-specific integrated circuits (ASIC) 609. A DSP 607 typically is configured to process real-world signals (e.g., sound) in real time independently of the processor 603. Similarly, an ASIC 609 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 603 and accompanying components have connectivity to the memory 605 via the bus 601. The memory 605 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 605 also stores the data associated with or generated by the execution of one or more steps of the methods described herein.

Figure 7:
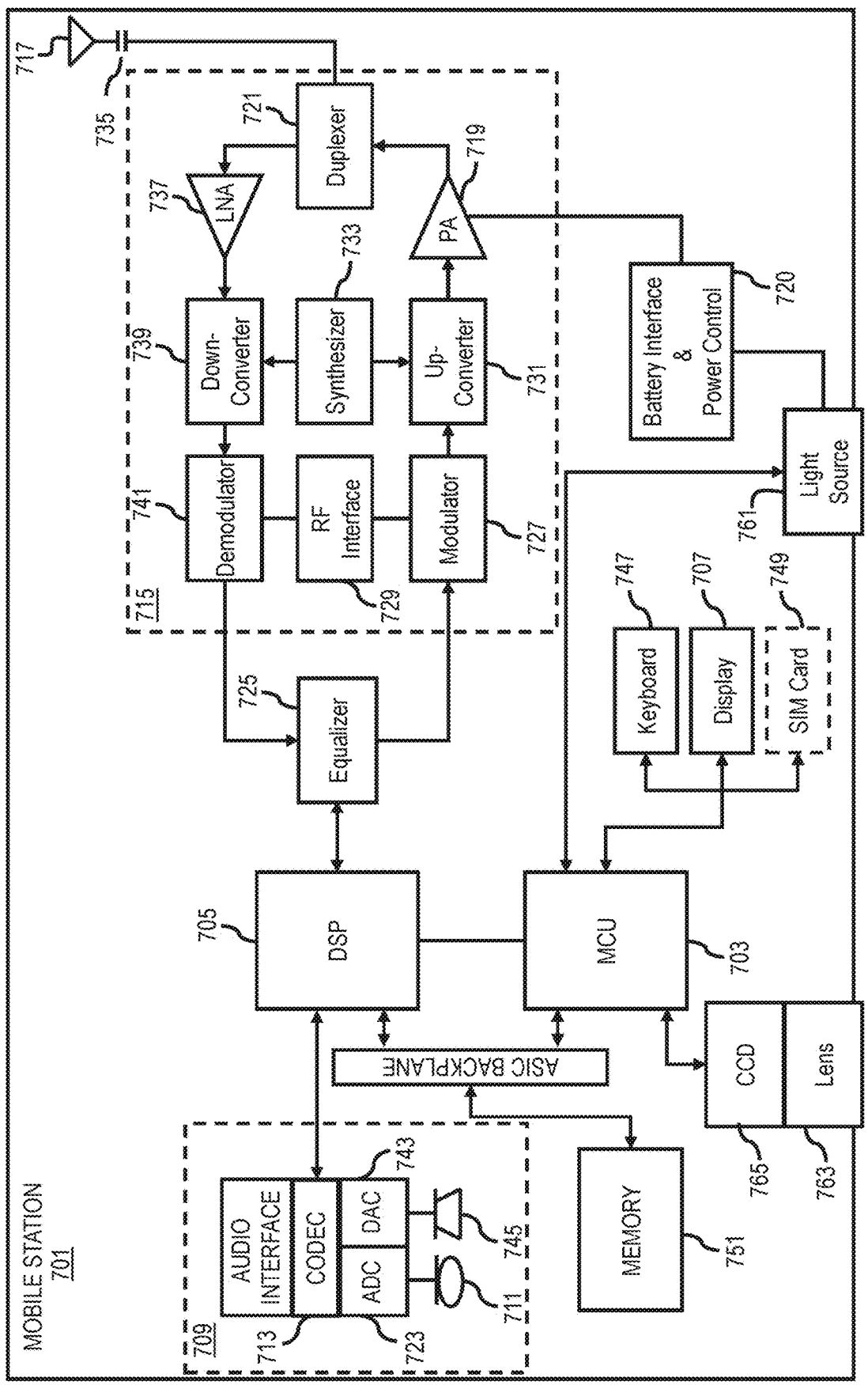
FIG. 7 is a diagram of example components of a mobile terminal (e.g., cell phone handset) for communications, which is capable of operating in the system, according to one embodiment.

FIG. 7 is a diagram of exemplary components of a mobile terminal 700 (e.g., cell phone handset) for communications, which is capable of operating in the system of FIG. 2C, according to one embodiment. In some embodiments, mobile terminal 701, or a portion thereof, constitutes a means for performing one or more steps described herein. Generally, a radio receiver is often defined in terms of front-end and back-end characteristics. The front-end of the receiver encompasses all of the Radio Frequency (RF) circuitry whereas the back-end encompasses all of the base-band processing circuitry. As used in this application, the term "circuitry" refers to both: (1) hardware-only implementations (such as implementations in only analog and/or digital circuitry), and (2) to combinations of circuitry and software (and/or firmware) (such as, if applicable to the particular context, to a combination of processor(s), including digital signal processor(s), software, and memory(ies) that work together to cause an apparatus, such as a mobile phone or server, to perform various functions). This definition of "circuitry" applies to all uses of this term in this application, including in any claims. As a further example, as used in this application and if applicable to the particular context, the term "circuitry" would also cover an implementation of merely a processor (or multiple processors) and its (or their) accompanying software/or firmware. The term "circuitry" would also cover if applicable to the particular context, for example, a baseband integrated circuit or applications processor integrated circuit in a mobile phone or a similar integrated circuit in a cellular network device or other network devices.

Pertinent internal components of the telephone include a Main Control Unit (MCU) 703, a Digital Signal Processor (DSP) 705, and a receiver/transmitter unit including a microphone gain control unit and a speaker gain control unit. A main display unit 707 provides a display to the user in support of various applications and mobile terminal functions that perform or support the steps as described herein. The display 707 includes display circuitry configured to display at least a portion of a user interface of the mobile terminal (e.g., mobile telephone). Additionally, the display 707 and display circuitry are configured to facilitate user control of at least some functions of the mobile terminal. An audio function circuitry 709 includes a microphone 711 and microphone amplifier that amplifies the speech signal output from the microphone 711. The amplified speech signal output from the microphone 711 is fed to a coder/decoder (CODEC) 713.

A radio section 715 amplifies power and converts frequency in order to communicate with a base station, which is included in a mobile communication system, via antenna 717. The power amplifier (PA) 719 and the transmitter/modulation circuitry are operationally responsive to the MCU 703, with an output from the PA 719 coupled to the duplexer 721 or circulator or antenna switch, as known in the art. The PA 719 also couples to a battery interface and power control unit 720.

In use, a user of mobile terminal 701 speaks into the microphone 711 and his or her voice along with any detected background noise is converted into an analog voltage. The analog voltage is then converted into a digital signal through the Analog to Digital Converter (ADC) 723. The control unit 703 routes the digital signal into the DSP 705 for processing therein, such as speech encoding, channel encoding, encrypting, and interleaving. In one embodiment, the processed voice signals are encoded, by units not separately shown, using a cellular transmission protocol such as enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., microwave access (WiMAX), Long Term Evolution (LTE) networks, code division multiple access (CDMA), wideband code division multiple access (WCDMA), wireless fidelity (WiFi), satellite, and the like, or any combination thereof.

The encoded signals are then routed to an equalizer 725 for compensation of any frequency-dependent impairments that occur during transmission though the air such as phase and amplitude distortion. After equalizing the bit stream, the modulator 727 combines the signal with a RF signal generated in the RF interface 729. The modulator 727 generates a sine wave by way of frequency or phase modulation. In order to prepare the signal for transmission, an up-converter 731 combines the sine wave output from the modulator 727 with another sine wave generated by a synthesizer 733 to achieve the desired frequency of transmission. The signal is then sent through a PA 719 to increase the signal to an appropriate power level. In practical systems, the PA 719 acts as a variable gain amplifier whose gain is controlled by the DSP 705 from information received from a network base station. The signal is then filtered within the duplexer 721 and optionally sent to an antenna coupler 735 to match impedances to provide maximum power transfer. Finally, the signal is transmitted via antenna 717 to a local base station. An automatic gain control (AGC) can be supplied to control the gain of the final stages of the receiver. The signals may be forwarded from there to a remote telephone which may be another cellular telephone, any other mobile phone or a land-line connected to a Public Switched Telephone Network (PSTN), or other telephony networks.

Voice signals transmitted to the mobile terminal 701 are received via antenna 717 and immediately amplified by a low noise amplifier (LNA) 737. A down-converter 739 lowers the carrier frequency while the demodulator 741 strips away the RF leaving only a digital bit stream. The signal then goes through the equalizer 725 and is processed by the DSP 705. A Digital to Analog Converter (DAC) 743 converts the signal and the resulting output is transmitted to the user through the speaker 745, all under control of a Main Control Unit (MCU) 703 which can be implemented as a Central Processing Unit (CPU) (not shown).

The MCU 703 receives various signals including input signals from the keyboard 747. The keyboard 747 and/or the MCU 703 in combination with other user input components (e.g., the microphone 711) comprise a user interface circuitry for managing user input. The MCU 703 runs a user interface software to facilitate user control of at least some functions of the mobile terminal 701 as described herein. The MCU 703 also delivers a display command and a switch command to the display 707 and to the speech output switching controller, respectively. Further, the MCU 703 exchanges information with the DSP 705 and can access an optionally incorporated SIM card 749 and a memory 751. In addition, the MCU 703 executes various control functions required of the terminal. The DSP 705 may, depending upon the implementation, perform any of a variety of conventional digital processing functions on the voice signals. Additionally, DSP 705 determines the background noise level of the local environment from the signals detected by microphone 711 and sets the gain of microphone 711 to a level selected to compensate for the natural tendency of the user of the mobile terminal 701.

The CODEC 713 includes the ADC 723 and DAC 743. The memory 751 stores various data including call incoming tone data and is capable of storing other data including music data received via, e.g., the global Internet. The software module could reside in RAM memory, flash memory, registers, or any other form of writable storage medium known in the art. The memory device 751 may be, but not limited to, a single memory, CD, DVD, ROM, RAM, EEPROM, optical storage, magnetic disk storage, flash memory storage, or any other non-volatile storage medium capable of storing digital data.

An optionally incorporated SIM card 749 carries, for instance, important information, such as the cellular phone number, the carrier supplying service, subscription details, and security information. The SIM card 749 serves primarily to identify the mobile terminal 701 on a radio network. The card 749 also contains a memory for storing a personal telephone number registry, text messages, and user specific mobile terminal settings.

In some embodiments, the mobile terminal 701 includes a digital camera comprising an array of optical detectors, such as charge coupled device (CCD) array 765. The output of the array is image data that is transferred to the MCU for further processing or storage in the memory 751 or both. In the illustrated embodiment, the light impinges on the optical array through a lens 763, such as a pin-hole lens or a material lens made of an optical grade glass or plastic material. In the illustrated embodiment, the mobile terminal 701 includes a light source 761, such as a LED to illuminate a subject for capture by the optical array, e.g., CCD 765. The light source is powered by the battery interface and power control module 720 and controlled by the MCU 703 based on instructions stored or loaded into the MCU 703.

3. Alternatives, Deviations and Modifications

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus, a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5× to 2×, for example, about 100 implies a value in a range from 50 to 200. Moreover, all ranges disclosed herein are to be understood to encompass any and all sub-ranges subsumed therein. For example, a range of "less than 10" for a positive only parameter can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

4. References

The references cited in the Appendix are hereby incorporated by reference as if fully set forth herein, except for terminology inconsistent with that used herein.

[1] C. A. Russo, C. Steiner, and W. Spector, "Hospitalizations related to pressure ulcers among adults 18 years and older, 2006: statistical brief #64," 2006, cost.

[2] "Preventing Pressure Ulcers in Hospitals," April 2011, cost. [Online]. Available: /professionals/systems/hospital/pressureulcertoolkit/index.html

[3] Hopkins Alison, Dealey Carol, Bale Sue, Defloor Tom, and Worboys Fran, "Patient stories of living with a pressure ulcer," Journal of Advanced Nursing, vol. 56, no. 4, pp. 345-353, September 2006, health Quality. [Online]. Available: https://onlinelibrary.wiley.com/doi/full/10.1111/j.1365-2648.2006.04007.x

[4] Gorecki Claudia, Brown Julia M., Nelson E. Andrea, Briggs Michelle, Schoonhoven Lisette, Dealey Carol, Defloor Tom, and Nixon Jane, "Impact of Pressure Ulcers on Quality of Life in Older Patients: A Systematic Review," Journal of the American Geriatrics Society, vol. 57, no. 7, pp. 1175-1183, June 2009, health Quality. [Online]. Available: https://onlinelibrary.wiley.com/doi/abs/10.1111/j.1532-5415.2009.02307.x

[5] B. Braden and N. Bergstrom, "A Conceptual Schema for the Study of the Etiology of Pressure Sores," Rehabilitation Nursing, vol. 12, no. 1, pp. 8-16, 1987, risk Factor Braden Scale.

[6] N. P. U. A. P. (US) and E. Haesler, Prevention and treatment of pressure ulcers: quick reference guide. Cambridge Media, 2014, nursing Guidelines.

[7] D. Norton, R. McLaren, and A. N. Exton-Smith, An investigation of geriatric nursing problems in hospital. Churchill Livingstone Edinburgh, 1962, risk Factor Norton.

[8] J. Waterlow, "Pressure sores: a risk assessment card." Nursing Times, vol. 81, no. 48, pp. 49-55, 1985, risk Factor Waterlow.

[9] M. T. Lowery, "A pressure sore risk calculator for intensive care patients: 'the Sunderland experience'," Intensive and Critical Care Nursing, vol. 11, no. 6, pp. 344-353, 1995, risk Factor Cubbin Jackson.

[10] J. P. Tran, J. M. McLaughlin, R. T. Li, and L. G. Phillips, "Prevention of Pressure Ulcers in the Acute Care Setting: New Innovations and Technologies," Plastic and Reconstructive Surgery, vol. 138, pp. 232S-240S, September 2016, survey Prevention. [Online]. Available: http://Insights.ovid.com/crossref?an=00006534-201609001-00030

[11] M. J. Peterson, W. Schwab, J. H. Van Oostrom, N. Gravenstein, and L. J. Caruso, "Effects of turning on skin-bed interface pressures in healthy adults," Journal of Advanced Nursing, vol. 66, no. 7, pp. 1556-1564, 2010, nursing Guidelines Not Enough.

[12] N. Gravenstein, J. H. van Oostrom PhD, and L. J. Caruso, "Patient repositioning and pressure ulcer risk-Monitoring interface pressures of at-risk patients," Journal of Rehabilitation Research and Development, vol. 50, no. 4, p. 477, 2013, nursing Guidelines Not Enough.

[13] NPUAP, "National Pressure Ulcer Advisory Panel Support Surface Standards Initiative," January 2007, definitions.

[14] E. McInnes, A. Jammali-Blasi, S. E. Bell-Syer, J. C. Dumville, V. Middleton, and N. Cullum, "Support surfaces for pressure ulcer prevention," Cochrane Database of Systematic Reviews, no. 9, pp. 1-119, 2015, support Surfaces Survey.

[15] S. Newbern, "Why your facility needs a full-time certified wound care nurse," Nursing, vol. 48, no. 2, pp. 66-68, February 2018, nurse Intervention. [Online]. Available: http://Insights.ovid.com/crossref?an=00152193-201802000-00016

[16] D. C. Shieh, C. M. Berringer, R. Pantoja, J. Resureccion, J. M. Rainbolt, and A. Hokoki, "Dramatic Reduction in Hospital-Acquired Pressure Injuries Using a Pink Paper Reminder System," Advances in Skin & Wound Care, vol. 31, no. 3, pp. 118-122, March 2018, nurse Intervention. [Online]. Available: http://Insights.ovid.com/crossref?an=00129334-201803000-00004

[17] T. M. Snavely, "A brief economic analysis of the looming nursing shortage in the United States," Nursing Economics, vol. 34, no. 2, p. 98, 2016, nursing Shortage.

[18] A. Siddiqui, R. Behrendt, M. Lafluer, S. Craft, and others, "A continuous bedside pressure mapping system for prevention of pressure ulcer development in the medical ICU: a retrospective analysis," Wounds, vol. 25, no. 12, pp. 333-339, 2013, cBPM.

[19] R. Behrendt, A. M. Ghaznavi, M. Mahan, S. Craft, and A. Siddiqui, "Continuous Bedside Pressure Mapping and Rates of Hospital-Associated Pressure Ulcers in a Medical Intensive Care Unit," American Journal of Critical Care, vol. 23, no. 2, pp. 127-133, March 2014, cBPM PMID: 24585161. [Online]. Available:http://ajcc.aacnjournals.org/content/23/2/127

[20] L. Gunningberg, I.-M. Sedin, S. Andersson, and R. Pingel, "Pressure mapping to prevent pressure ulcers in a hospital setting: A pragmatic randomised controlled trial," International Journal of Nursing Studies, vol. 72, pp. 53-59,2017, cBPM.

[21] D. Pickham, N. Berte, M. Pihulic, A. Valdez, B. Mayer, and M. Desai, "Effect of a wearable patient sensor on care delivery for preventing pressure injuries in acutely ill adults: A pragmatic randomized clinical trial (LS-HAPI study)," International Journal of Nursing Studies, vol. 80, pp. 12-19,2018, accelerometer.

[22] J. B. Reswick and J. E. Rogers, "Experience at Rancho Los Amigos Hospital with devices and techniques to prevent pressure sores," in Bed sore biomechanics. Springer, 1976, pp. 301-310.

[23] M. Farshbaf, R. Yousefi, M. B. Pouyan, S. Ostadabbas, M. Nourani, and M. Pompeo, "Detecting high-risk regions for pressure ulcer risk assessment," in Bioinformatics and Biomedicine (BIBM), 2013 IEEE International Conference on. IEEE, 2013, pp. 255-260, posture Detection Limb-Identification.

[24] S. Ostadabbas, M. B. Pouyan, M. Nourani, and N. Kehtarnavaz, "In-bed posture classification and limb identification," in Biomedical Circuits and Systems Conference (BioCAS), 2014 IEEE. IEEE, 2014, pp. 133-136, posture Detection Limb-Identification. [Online]. Available: http://ieeexplore.ieee.org/abstract/document/6981663/

[25] J. J. Liu, M.-C. Huang, W. Xu, and M. Sarrafzadeh, "Bodypart localization for pressure ulcer prevention," in Engineering in Medicine and Biology Society (EMBC), 2014 36th Annual International Conference of the IEEE. IEEE, 2014, pp. 766-769, posture Detection Limb-Identification.

[26] M. B. Pouyan, M. Nourani, and M. Pompeo, "Clustering-based limb identification for pressure ulcer risk assessment," in Engineering in Medicine and Biology Society (EMBC), 2015 37th Annual International Conference of the IEEE. IEEE, 2015, pp. 4230-4233, posture Detection Limb-Identification.

[27] M. B. Pouyan, J. Birjandtalab, M. Nourani, and M. M. Pompeo, "Automatic limb identification and sleeping parameters assessment for pressure ulcer prevention," Computers in Biology and Medicine, vol. 75, pp. 98-108, 2016, posture Detection Limb-Identification.

[28] Z. Moore, D. Patton, S. L. Rhodes, and T. O'Connor, "Subepidermal moisture (SEM) and bioimpedance: a literature review of a novel method for early detection of pressure-induced tissue damage (pressure ulcers)," International Wound Journal, vol. 14, no. 2, pp. 331-337, 2016, skin Sensing. [Online]. Available: https://onlinelibrary.wiley.com/doi/abs/10.1111/iwj.12604

[29] S. L. Swisher, M. C. Lin, A. Liao, E. J. Leeflang, Y. Khan, F. J. Pavinatto, K. Mann, A. Naujokas, D. Young, S. Roy, and others, "Impedance sensing device enables early detection of pressure ulcers in vivo," Nature Communications, vol. 6, p. ncomms7575, 2015, skin Sensing Sentinel.

[30] M. F. Farooqui and A. Shamim, "Low Cost Inkjet Printed Smart Bandage for Wireless Monitoring of Chronic Wounds," Scientific Reports, vol. 6, p. 28949, June 2016, skin Sensing. [Online]. Available: https://www.nature.com/articles/srep28949

[31] S. Mansfield, K. Obraczka, and S. Roy, "Pressure Injury Prevention: A Survey," IEEE Reviews In Biomedical Engineering, pp. 1-3, 2019, survey.

[32] F. P. García-Fernández, J. Agreda, J. Verdú, and P. L. Pancorbo-Hidalgo, "A New Theoretical Model for the Development of Pressure Ulcers and Other Dependence-Related Lesions," Journal of Nursing Scholarship, vol. 46, no. 1, pp. 28-38, 2014, risk Factors. [Online]. Available: http://onlinelibrary.wiley.com.oca.ucsc.edu/doi/10.1111/jnu.12051/full

[33] J. Alderden, J. Rondinelli, G. Pepper, M. Cummins, and J. Whitney, "Risk factors for pressure injuries among critical care patients: A systematic review," International Journal of Nursing Studies, vol. 71, pp. 97-114, June 2017, risk Factors. [Online]. Available: http://www.sciencedirect.com/science/article/pii/S0020748917300858

What is claimed is:

1. A method for patient pressure injury prevention (PPIP) comprising:
   receiving, from a plurality of pressure sensors in a wearable pressure array configured to be worn by a patient, samples data that indicate pressure measurements by the plurality of sensors at each of a plurality of different times;
   computing a pressure plane based on the pressure measurements from the pressure array, with the pressure plane being defined in 3D space;
   determining a direction of the pressure plane which corresponds to an orientation of the patient, with the direction being perpendicular to a face of the pressure plane;
   determining at each of the plurality of different times an angular orientation of the pressure plane based on a strength and the direction of the pressure plane;
   determining a value of a patient movement parameter based on a history of the strength of movement or a total number of movements over a time interval, with the patient movement parameter corresponding to a condition of the patient;
   presenting on a display device a pressure injury category for the patient corresponding to the value of the patient movement parameter, with the patient's risk of pressure injury or need for assisted movement being presented as a time series over the time interval; and
   recommending treatment for assisting the patient in changing posture or moving based on the displayed pressure injury category.

2. The method as recited in claim 1, wherein the spatial arrangement of the plurality of pressure sensors is a two dimensional array such as a 4×4 array.

3. The method as recited in claim 1, wherein the contact with the patient is contact with a surface of the patient in a vicinity of a sacrum of the patients.

4. The method as recited in claim 1, wherein the angular orientation is a pressure plane determined by three pressure values based on the samples.

5. The method as recited in claim 4, wherein each of the three pressure values is an average of samples from a different one of three different subsets of the plurality of pressure sensors.

6. The method as recited in claim 5, wherein a union of the three different subsets include all of the plurality of pressure sensors.

7. The method as recited in claim 5, wherein no pressure sensor is in more than one subset of the three different subsets.

8. The method as recited in claim 5, wherein each pressure sensor in one subset is adjacent to another pressure sensor in the one subset.

9. The method as recited in claim 1, wherein the angular orientation is a posture of the patient.

10. The method as recited in claim 1, wherein a movement is a change in angular orientation greater than a threshold change and the patient movement parameter is based on a movement.

11. The method as recited in claim 10, wherein the patient movement parameter is a number of movements per unit time.

12. The method as recited in claim 10, wherein the patient movement parameter is a size of the movement.

13. The method as recited in claim 10, wherein the treatment includes movement of the patient by the caregiver at a time based on the pressure injury category.

14. The method as recited in claim 1, further comprising a manual step of disposing the plurality of pressure sensors in contact with the patient.

15. A non-transitory computer-readable medium carrying one or more sequences of instructions for patient pressure injury monitoring and prevention (PIMAP), wherein execution of the one or more sequences of instructions by one or more processors causes the one or more processors to perform:
   computing a pressure plane based on the pressure measurements from the pressure array, with the pressure plane being defined in 3D space;
   determining a direction of the pressure plane which corresponds to an orientation of the patient, with the direction being perpendicular to a face of the pressure plane;
   determining at each of the plurality of different times an angular orientation of the pressure plane based on a strength and the direction of the pressure plane;
   determining a strength of movement or a rate of movement of the patient in response to the change in the direction of the pressure plane that exceeds an angular threshold;
   determining a value of a patient movement parameter based on a history of the strength of movement or a total number of movements over a time interval, with the patient movement parameter corresponding to a condition of the patient;
   presenting on a display device a pressure injury category for the patient corresponding to the value of the patient movement parameter, with the patient's risk of pressure injury or need for assisted movement being presented as a time series over the time interval, which is used for recommending treatment to the patient by a caregiver by assisting the patient in changing posture or moving.

16. An apparatus for patient pressure injury prevention (PPIP) comprising:
   at least one processor; and
   at least one memory including one or more sequences of instructions,
   the at least one memory and the one or more sequences of instructions configured to, with the at least one processor, cause the apparatus to perform:
      computing a pressure plane based on the pressure measurements from the pressure array, with the pressure plane being defined in 3D space;
      determining a direction of the pressure plane which corresponds to an orientation of the patient, with the direction being perpendicular to a face of the pressure plane;
      determining at each of the plurality of different times an angular orientation of the pressure plane based on a strength and the direction of the pressure plane;
      determining a strength of movement or a rate of movement of the patient in response to the change in the direction of the pressure plane that exceeds an angular threshold;
      determining a value of a patient movement parameter based on a history of the strength of movement or a total number of movements over a time interval, with the patient movement parameter corresponding to a condition of the patient;
      presenting on a display device a pressure injury category for the patient corresponding to the value of the patient movement parameter, with the patient's risk of pressure injury or need for assisted movement being presented as a time series over the time interval, which is used for recommending treatment to the patient by a caregiver by assisting the patient in changing posture or moving.

17. A system for patient pressure injury prevention (PPIP) comprising:
   a plurality of pressure sensors configured to be disposed in a spatial arrangement in contact with a patient;
   a display device;
   at least one processor; and
   at least one memory including one or more sequences of instructions,
   the at least one memory and the one or more sequences of instructions configured to, with the at least one processor, perform:
      computing a pressure plane based on the pressure measurements from the pressure array, with the pressure plane being defined in 3D space;
      determining a direction of the pressure plane which corresponds to an orientation of the patient, with the direction being perpendicular to a face of the pressure plane;
      determining at each of the plurality of different times an angular orientation of the pressure plane based on a strength and the direction of the pressure plane;
      determining a strength of movement or a rate of movement of the patient in response to the change in the direction of the pressure plane that exceeds an angular threshold;
      determining a value of a patient movement parameter based on a history of the strength of movement or a total number of movements over a time interval, with the patient movement parameter corresponding to a condition of the patient;
      presenting on a display device a pressure injury category for the patient corresponding to the value of the patient movement parameter, with the patient's risk of pressure injury or need for assisted movement being presented as a time series over the time interval, which is used for recommending treatment to the patient by a caregiver by assisting the patient in changing posture or moving.

18. The system as recited in claim 17, wherein the spatial arrangement of the plurality of pressure sensors is a 4×4 array.

19. The system as recited in claim 17, wherein the contact with the patient is contact with a surface of the patient in a vicinity of a sacrum of the patient.

* * * * *